United States Patent
Cunningham et al.

(10) Patent No.: US 8,407,095 B2
(45) Date of Patent: *Mar. 26, 2013

(54) METHOD OF DELIVERING A PHARMACEUTICAL PRODUCT VIA A MEDIUM

(75) Inventors: David W. Cunningham, Raleigh, NC (US); John M. Harden, Oxford, NC (US); William N. Engle, Raleigh, NC (US); Charles W. Reuben, Cary, NC (US)

(73) Assignee: Trialcard Incorporated, Cary, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/209,970

(22) Filed: Aug. 15, 2011

(65) Prior Publication Data

US 2011/0301973 A1    Dec. 8, 2011

Related U.S. Application Data

(60) Continuation of application No. 11/459,070, filed on Jul. 21, 2006, now Pat. No. 8,055,542, which is a division of application No. 10/098,700, filed on Mar. 15, 2002, now Pat. No. 7,925,531, which is a continuation-in-part of application No. 09/558,260, filed on Apr. 25, 2000, now Pat. No. 6,859,780.

(51) Int. Cl.
G06Q 20/00 (2012.01)

(52) U.S. Cl. ............................... 705/17; 705/18; 705/16

(58) Field of Classification Search .............. 705/16–18
See application file for complete search history.

(56) References Cited

U.S. PATENT DOCUMENTS

| | | |
|---|---|---|
| 3,845,278 A | 10/1974 | Rex, Jr. |
| 4,195,864 A | 4/1980 | Morton et al. |
| 4,695,954 A | 9/1987 | Rose et al. |
| 4,695,956 A | 9/1987 | LeVeen |
| 4,778,153 A | 10/1988 | Bachman et al. |
| 4,827,112 A | 5/1989 | Yoshino et al. |
| 4,855,578 A | 8/1989 | Hirokawa et al. |
| 4,857,716 A | 8/1989 | Gombrich et al. |
| 4,893,270 A | 1/1990 | Beck et al. |
| 4,908,761 A | 3/1990 | Tai |
| 4,971,362 A | 11/1990 | Lapsker |
| 4,971,632 A | 11/1990 | Rowe |

(Continued)

FOREIGN PATENT DOCUMENTS

| | | |
|---|---|---|
| EP | 0354260 A1 | 2/1990 |
| WO | 9303457 | 7/1991 |

(Continued)

OTHER PUBLICATIONS

Final Rejection dated Sep. 13, 2012, U.S. Appl. No. 13/108,139, filed May 16, 2011.

(Continued)

*Primary Examiner* — Ramsey Refai
(74) *Attorney, Agent, or Firm* — Coats & Bennett, P.L.L.C.

(57) ABSTRACT

One or more embodiments include a method of delivering a pharmaceutical product via a medium. The pharmaceutical product is associated with the medium and the medium assumes different values based on predetermined business rules. The method includes generating data in a database associated with a central computing station where the data identifies the medium and the product associated with the medium. The database is provisioned with the rules that determine the value of the medium. In response to the holder presenting the medium to a provider of the product for purposes of obtaining the product, a communication from the provider is received identifying the medium. A value for the medium is established based on the rules provisioned in the database. The value of the medium is updated, and that updated value is recorded in the database in response to the provider providing the product to the holder of the medium.

11 Claims, 27 Drawing Sheets

U.S. PATENT DOCUMENTS

| | | | |
|---|---|---|---|
| 5,048,870 | A | 9/1991 | Mangini et al. |
| 5,181,743 | A | 1/1993 | Lloyd |
| 5,192,854 | A | 3/1993 | Counts |
| 5,317,506 | A | 5/1994 | Coutre et al. |
| 5,542,420 | A | 8/1996 | Goldman et al. |
| 5,577,109 | A | 11/1996 | Stimson et al. |
| 5,577,197 | A | 11/1996 | Beck |
| 5,612,870 | A | 3/1997 | Welner |
| 5,628,530 | A | 5/1997 | Thornton |
| 5,644,723 | A | 7/1997 | Deaton et al. |
| 5,664,109 | A | 9/1997 | Johnson et al. |
| 5,671,282 | A | 9/1997 | Wolff et al. |
| 5,673,402 | A | 9/1997 | Ryan et al. |
| 5,682,027 | A | 10/1997 | Bertina |
| 5,710,886 | A | 1/1998 | Christensen et al. |
| 5,737,539 | A | 4/1998 | Edelson et al. |
| 5,758,095 | A | 5/1998 | Albaum et al. |
| 5,774,357 | A | 6/1998 | Hoffberg et al. |
| 5,777,305 | A | 7/1998 | Smith et al. |
| 5,799,981 | A | 9/1998 | Tung et al. |
| 5,803,498 | A | 9/1998 | Tung et al. |
| 5,822,544 | A | 10/1998 | Chaco et al. |
| 5,832,449 | A | 11/1998 | Cunningham |
| 5,845,255 | A | 12/1998 | Mayaud |
| 5,867,821 | A | 2/1999 | Ballantyne et al. |
| 5,875,431 | A | 2/1999 | Heckman et al. |
| 6,000,608 | A | 12/1999 | Dorf |
| 6,041,309 | A | 3/2000 | Laor |
| 6,138,106 | A | 10/2000 | Walker et al. |
| 6,208,973 | B1 | 3/2001 | Boyer et al. |
| 6,249,809 | B1 | 6/2001 | Bro |
| 6,292,785 | B1 | 9/2001 | McEvoy et al. |
| 6,314,406 | B1 | 11/2001 | O'Hagan et al. |
| 6,321,208 | B1 | 11/2001 | Barnett et al. |
| 6,349,134 | B1 | 2/2002 | Katz |
| 6,404,866 | B1 | 6/2002 | Hopper et al. |
| 6,467,684 | B2 | 10/2002 | Fite et al. |
| 6,505,171 | B1 | 1/2003 | Cohen et al. |
| 6,575,361 | B1 | 6/2003 | Graves et al. |
| 6,865,547 | B1 | 3/2005 | Brake, Jr. et al. |
| 6,970,851 | B1 | 11/2005 | Goodwin, III et al. |
| 6,988,075 | B1 | 1/2006 | Hacker |
| 7,006,214 | B2 | 2/2006 | Rzasa et al. |
| 7,398,248 | B2 | 7/2008 | Phillips et al. |
| 7,444,305 | B2 | 10/2008 | Cotten et al. |
| 7,512,566 | B1 | 3/2009 | Fellner |
| 2003/0036923 | A1 | 2/2003 | Waldon et al. |

FOREIGN PATENT DOCUMENTS

| | | |
|---|---|---|
| WO | 0109701 | 2/2001 |

OTHER PUBLICATIONS

Non-Final Rejection dated Sep. 5, 2012, U.S. Appl. No. 13/402,218, filed Feb. 22, 2012.

Final Rejection dated Sep. 17, 2012, U.S. Appl. No. 13/084,188, filed Apr. 11, 2011.

Amendment and Extension of Time filed Jul. 26, 2012, U.S. Appl. No. 13/329,797, filed Dec. 19, 2011.

Final Rejection dated Sep. 12, 2012, U.S. Appl. No. 13/329,797, filed Dec. 19, 2011.

Office Action dated Sep. 12, 2012, Inter Partes Reexamination, U.S. Appl. No. 95/002,029, filed Jun. 22, 2012.

Promo Staff. "Answering the Call." [online] Promo Magazine, Dec. 1, 2000 [retrieved on May 21, 2012]. Retrieved from the Internet:<URL: http://chiefmarketer.com/mag/marketing_answering_call>.

Defendants' Invalidity Contentions with Exhibits A and B, *Trialcard Incorporated* v. *Medimedia Usa, Inc./Trialcard Incorporation* v. *PSKW, LLC*, United States District Court for the District of New Jersey, Case Nos. 3:11-CV-5693 (FLW)(TJB) and 3:11-CV-7341 (FLW)(TJB) filed May 24, 2012.

Request for Inter Partes Reexamination of U.S. Patent No. 7,925,531 Pursuant to 35 U.S.C. Sections 311-318 and 37 C.F.R. Section 1.915, Patent No. 7,925,531 Issued Apr. 12, 2011, U.S. Appl. No. 10/098,700, filed Mar. 15, 2002, entitled "Method of Delivering Goods and Services via Media".

Non-Final Rejection dated Apr. 12, 2012, U.S. Appl. No. 13/329,797, filed Dec. 19, 2011.

Non-Final Rejection dated Mar. 21, 2012, U.S. Appl. No. 13/108,139, filed May 16, 2011.

Response to Non-Final Rejection dated Jun. 20, 2012, U.S. Appl. No. 13/108,139, filed May 16, 2011.

Non-Final Rejection dated Mar. 20, 2012, U.S. Appl. No. 13/084,188, filed Apr. 11, 2011.

Response to Non-Final Rejection dated Jun. 20, 2012, U.S. Appl. No. 13/084,188, filed Apr. 11, 2011.

Non-Final Rejection dated Aug. 19, 2008, U.S. Appl. No. 11/459,082, filed Jul. 21, 2006.

Response to Non-Final Rejection dated Jan. 6, 2009, U.S. Appl. No. 11/459,082, filed Jul. 21, 2006.

Final Rejection dated May 26, 2009, U.S. Appl. No. 11/459,082, filed Jul. 21, 2006.

Non-Final Rejection dated Nov. 24, 2009, U.S. Appl. No. 11/459,082, filed Jul. 21, 2006.

Appeal Brief dated Aug. 27, 2010, U.S. Appl. No. 11/459,082, filed Jul. 21, 2006.

Examiner's Answer to Appeal Brief dated Nov. 9, 2010, U.S. Appl. No. 11/459,082, filed Jul. 21, 2006.

Reply Brief dated Jan. 7, 2011, U.S. Appl. No. 11/459,082, filed Jul. 21, 2006.

Non-Final Rejection dated Oct. 29, 2009, U.S. Appl. No. 11/459,062, filed Jul. 21, 2006.

Response to Non-Final Rejection dated Dec. 16, 2009, U.S. Appl. No. 11/459,062, filed Jul. 21, 2006.

Final Rejection dated Mar. 30, 2010, U.S. Appl. No. 11/459,062, filed Jul. 21, 2006.

Amendment-After-Final Rejection dated Jul. 14, 2010, U.S. Appl. No. 11/459,062, filed Jul. 21, 2006.

Non-Final Rejection dated Aug. 2, 2010, U.S. Appl. No. 11/459,062, filed Jul. 21, 2006.

Response to Non-Final Rejection dated Aug. 25, 2010, U.S. Appl. No. 11/459,062, filed Jul. 21, 2006.

Final Rejection dated Apr. 28, 2011, U.S. Appl. No. 11/459,062, filed Jul. 21, 2006.

Appeal Brief dated Nov. 15, 2011, U.S. Appl. No. 11/459,062, filed Jul. 21, 2006.

Examiner's Answer to Appeal Brief dated Jan. 18, 2012, U.S. Appl. No. 11/459,062, filed Jul. 21, 2006.

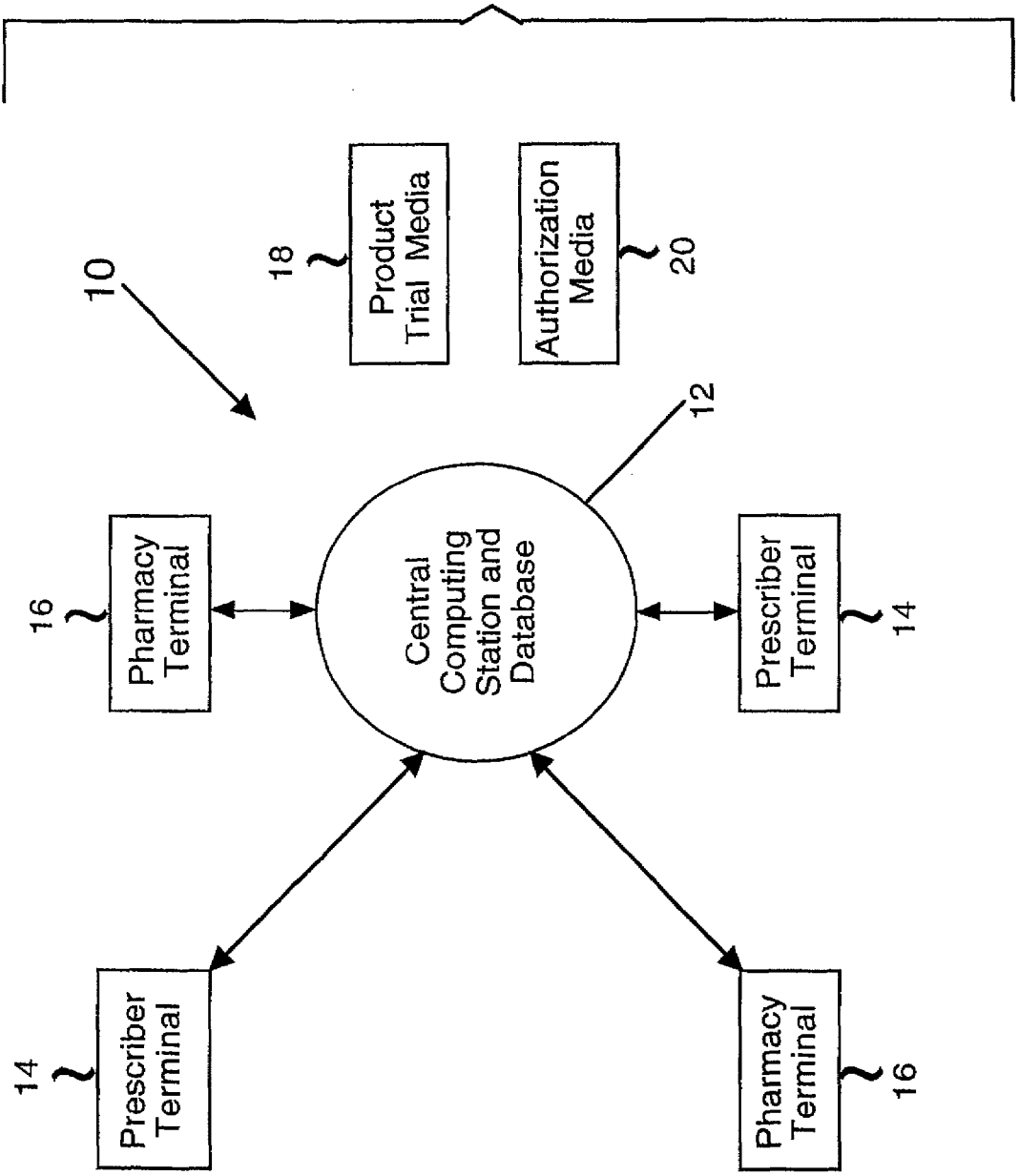

Figure 2B

Physician Approval Code
Pharmacist Approval Code
Physician Signature
Pharmacist Signature
Patient Signature

Authorizer Signature

TRIAL PRODUCT TRADE NAME
TRIAL PRODUCT GENERIC NAME
TRIAL PRODUCT FORM & STRENGTH
TRIAL PRODUCT QUANTITY

CARD SERIAL NUMBER
CARD EXPIRATION DATE

AUTHORIZER ID NUMBER

AUTHORIZER NAME
CARD EXPIRATION DATE

20

METHOD OF DELIVERING A PHARMACEUTICAL PRODUCT VIA A MEDIUM

RELATED APPLICATIONS

The present application is a continuation of U.S. patent application Ser. No. 11/459,070 filed Jul. 21, 2006, now U.S. Pat. No. 8,055,542, which is a divisional of U.S. patent application Ser. No. 10/098,700 filed Mar. 15, 2002, now U.S. Pat. No. 7,925,531, which is a continuation-in-part of U.S. patent application Ser. No. 09/558,260 filed Apr. 25, 2000, now U.S. Pat. No. 6,859,780, the disclosures of all of which are hereby expressly incorporated by reference.

FIELD OF THE INVENTION

The present invention relates generally to the distribution of pharmaceutical products and more particularly to an improved method of dispensing, tracking, and managing pharmaceutical products by communicatively linking prescribers and pharmacies to a central computing station in such a manner that variable values may be provided to different individuals based on selected variables such as location and/or volume purchased.

BACKGROUND OF THE INVENTION

In the pharmaceutical industry, the primary method for product promotion of ethical products is the use of outside sales representatives. Company sales representatives target specific physicians and detail the features and benefits of particular pharmaceutical products. Pharmaceutical manufacturers have documented that the most effective method of product promotion involves providing pharmaceutical product samples to prescribers of the products who then pass along the product samples to patients. Physicians therefore receive numerous quantities of pharmaceutical product samples for purposes of conducting patient trials. These trials enable physicians to determine the effectiveness of certain drugs in certain patients for certain diseases, as well as to determine patients' tolerance of the drugs and their compliance with drug administration directions.

A responsibility of the Food & Drug Administration (FDA) is the regulation of pharmaceutical product samples. The PDMA (Pharmaceutical Drug Manufacturing Act) Act of 1987 requires pharmaceutical manufacturers to track and account for product samples distributed by sales representatives to prescribing physicians. Pharmaceutical manufacturers are required to account for all sample product inventories, as well as the time, location, and specific physicians who receive promotional samples. Pharmaceutical sales representatives are required to record receipts of product samples, adjustments to sample inventories, and distribution of product samples, and to report any loss or theft of product samples. Additionally, PDMA warehousing requirements dictate inventory storage methods and locations both within pharmaceutical companies themselves and for outside pharmaceutical sales representatives.

However, it is often the case that accountability for pharmaceutical product samples ends when the samples reach the physicians. Most physicians do little to account for their inventories of product samples. Rather, physicians tend to distribute pharmaceutical product samples to patients much more informally than retail pharmacies, keeping few if any records and often not even counting the precise number of product samples given to patients.

The PDMA's accountability requirements increase pharmaceutical manufacturers' expenses for promoting and distributing product samples as well as the complexity of administering sampling programs. As competition within the pharmaceutical industry increases, costs associated with product samples place an increasingly greater burden on the pharmaceutical manufacturers. Pharmaceutical manufacturers are therefore attempting to reduce expenses and maintain acceptable profits while incorporating the PDMA's new requirements into established promotional practices.

Although product samples are an extremely effective promotional tool, the manufacturing of drug product samples in addition to normally packaged drug products has proven to be increasingly costly. Pharmaceutical product samples are typically elaborately and expensively packaged and are extremely bulky compared to normally packaged drug products. Pharmaceutical manufacturers utilize separate product sample packaging lines to package drug product samples. Distribution of product samples requires delivery via separate carriers and distribution routes. In addition, drug product samples are typically warehoused separately from normally packaged drug products.

Because the current climate in the pharmaceutical industry prohibits the unrestrained shifting of costs to final consumers, pharmaceutical manufacturers have taken several new approaches to reducing costs associated with promoting product samples. Nevertheless, pharmaceutical manufacturers are attempting to maintain the marketing advantages of using sales representatives to distribute product samples.

One cost-reducing approach that pharmaceutical manufacturers have attempted is the distribution of sample vouchers to prescribing physicians, retail pharmacies, and pharmaceutical sales representatives. With this approach, instead of giving drug product samples directly to patients, physicians give the patients vouchers for the drug product samples. The vouchers may then be redeemed at retail pharmacies for the actual drugs. Alternately, the patients may receive cash or credit rebates at the pharmacies.

Another cost-reducing approach that pharmaceutical manufacturers have attempted is the distribution of product samples via mail order. With this approach, pharmaceutical sales representatives provide prescribing physicians with request authorization forms. Physicians then use the forms to authorize deliveries of product samples directly to the physician's office from third-party pharmaceutical supply warehouses.

These approaches to distributing pharmaceutical product samples have not met with substantial and universal acceptance. All of these approaches lack an effective, efficient and practical system for distributing the trial or sample products to patients and at the same time recording pertinent data, which is easily accessible, relating to prescribing and dispensing the pharmaceutical trial products.

Additionally, there are strict rules associated with the dispensing of pharmaceuticals outside of the sample context. In particular, prescriptions are closely monitored by the appropriate government agencies. To help combat prescription fraud, new systems must be developed that allow prescription drugs to be tracked such that appropriate reporting may be performed about the dispensation of prescription drugs outside the sample context. Thus, there remains a need for alternative prescription routines that address these needs.

SUMMARY OF THE INVENTION

The present invention entails a method of delivering one or more goods or services via a medium. The method includes identifying one or more goods or services that may be received by a holder of the medium in response to the medium being presented to a provider of the identified goods or services. Each medium is uniquely identified and recorded in a database such that the goods or services associated with each medium can be identified. Initially, the medium assumes an inactive state. Prior to the medium being redeemed for goods or services, the media is activated which essentially means that its status changes from an inactive state to an active state. Thereafter, the medium can be presented to a provider of goods or services associated with the medium where the provider delivers at least one good or service associated with the medium to the holder presenting the medium. The method further includes communicating with the database and recording information in the database that describes the goods or services provided or delivered.

In another embodiment of the present invention, the database is programmed or provisioned such that the media may be assigned a variable value. That is, the value of the media can vary depending upon certain circumstances, conditions or criteria. For example, in various embodiments the value of the media or medium is a function of geography, manner of activation, time, or other user activity.

Further, in another embodiment, a medium or media may be distributed to an assignee. Prior to activation, the assignee, or another individual, communicates with the database in such a manner that the identity of the assignee is recorded along with the identity of the media being assigned to the assignee.

BRIEF DESCRIPTION OF THE DRAWINGS

FIG. 1 is a schematic illustration of the system of the present invention for managing the distribution of pharmaceutical trial products.

FIG. 2A is a front side view of the pharmaceutical trial product media that forms a part of the present invention.

FIG. 2B is a back side view of the pharmaceutical trial media.

FIG. 3A is a front side view of the authorization media that forms a part of the present invention.

FIG. 3B is a back side view of the authorization media.

DETAILED DESCRIPTION OF THE INVENTION

Figure 4A:
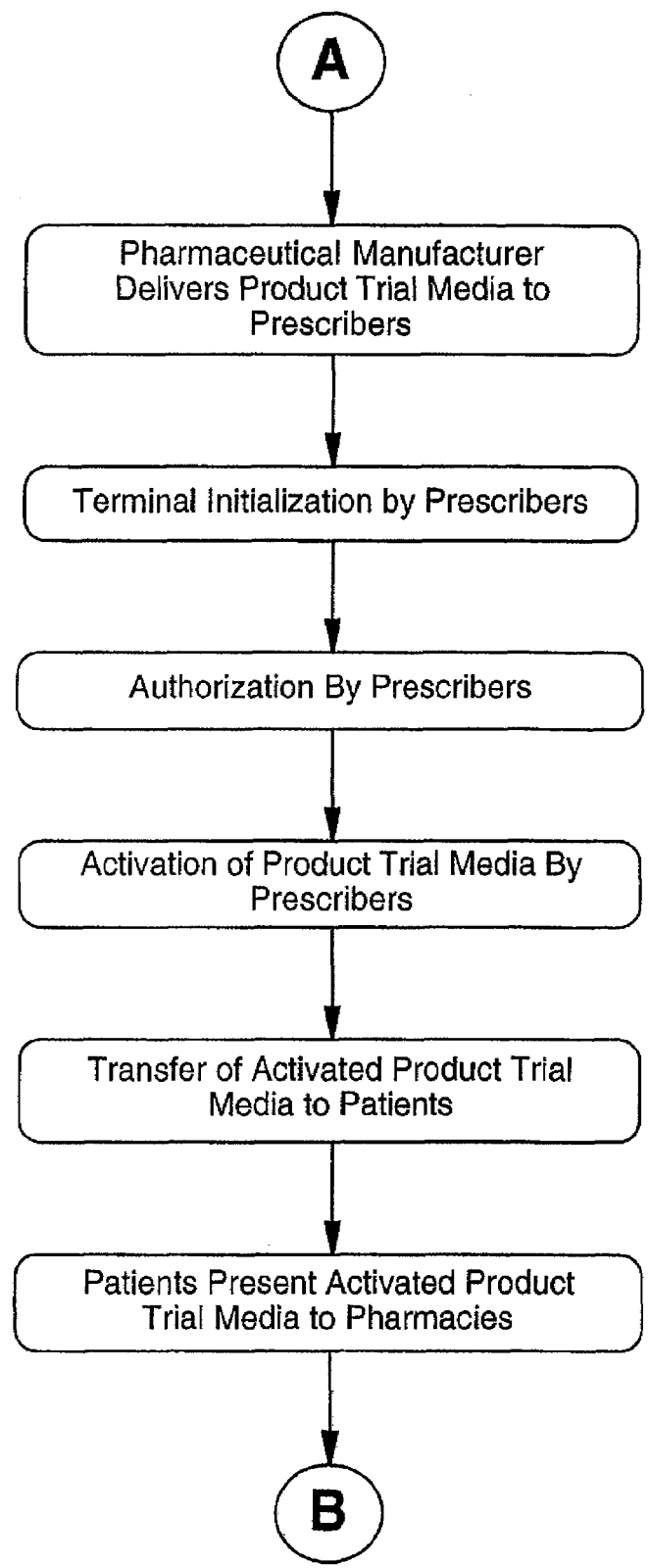
FIGS. 4A-4B depicts a flow chart that shows the basic steps entailed in distributing, tracking and managing pharmaceutical trial product distributed in accordance with the present invention.
Figure 4B:
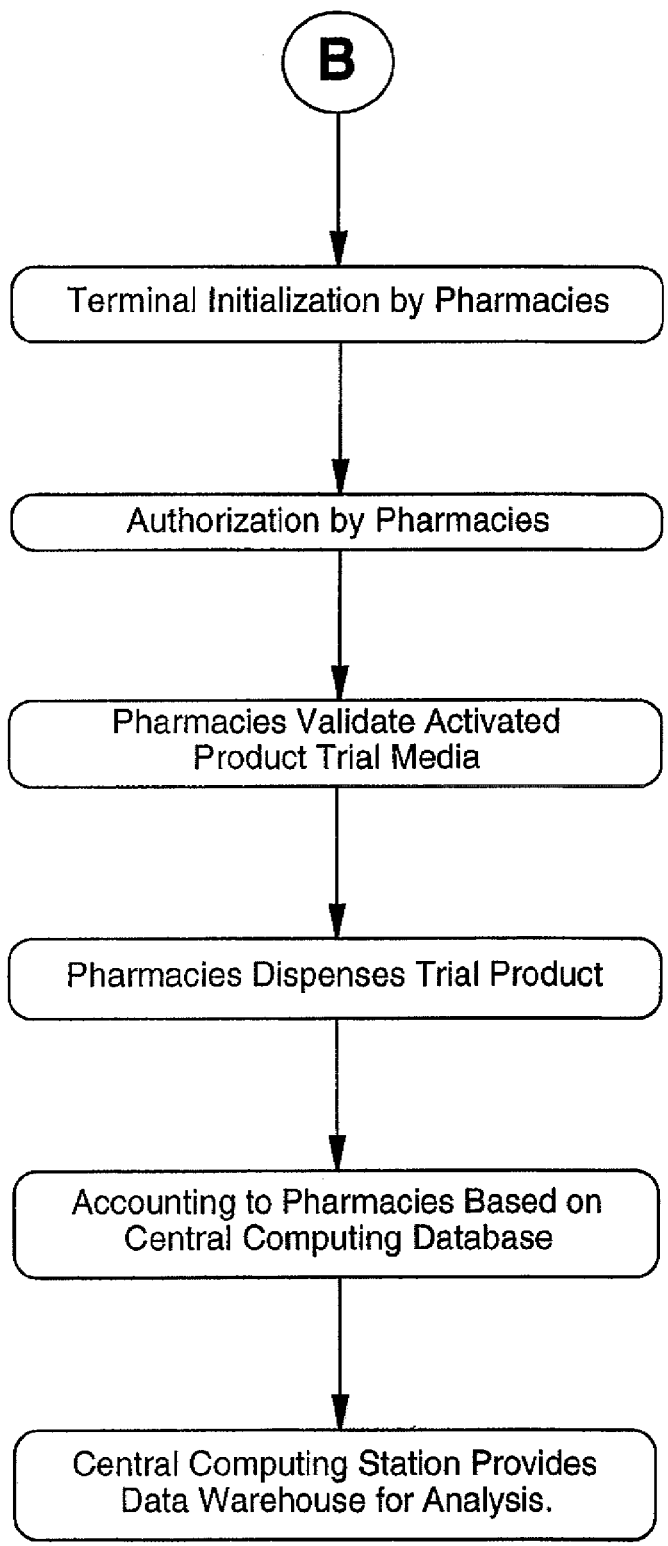

With further reference to the drawings and particularly to FIG. 1, the system utilized for carrying out the present invention is shown therein and indicated generally by the numeral 10. System 10 includes a central computing station 12 that has associated therewith a database for storing data and information communicated to the central computing station 12 during various steps or phases of the pharmaceutical trial product distribution process. As will be appreciated from subsequent portions of this disclosure, the present invention contemplates the utilization of participating medical doctors or prescribers and pharmacies to effectuate the distribution of pharmaceutical trial products. To communicate with the central computing station 12, each participating prescriber and pharmacy is provided with a terminal communicatively linked with the central computing station 12. Therefore, it is appreciated that the system 10 of the present invention will include prescriber terminals 14 located at various participating prescriber sites and pharmacy terminals 16 located at various participating pharmacy sites. Both the prescriber terminals 14 and the pharmacy terminals 16 are capable of communicatively linking encoded media with the central computing station 12 where the encoded information associated with the media can be recorded in the associated database. Various types of communication terminals can be utilized at prescriber and pharmacy sites. However, as will be appreciated from subsequent portions of this disclosure, one such type of terminal is a conventional magnetic card reader that is adapted to accept magnetic cards and to read or interpret encoded information provided thereon and to communicate with the central computing station 12.

System 10 further includes what is referred to as a pharmaceutical product trial media that in FIG. 1 is indicated by the numeral 18. As will be appreciated from subsequent portions of the disclosure, the product trial media 18 identifies and is associated with a particular pharmaceutical trial product and is transferred and passed between participating prescribers, patients and pharmacies. The product trial media 18 is particularly encoded with pertinent information that identifies a particular pharmaceutical trial product and is designed to be compatible with the prescriber and pharmacy terminals 14 and 16. In particular, prescriber and pharmacy terminals 14 and 16 are capable of reading the product trial media 18 and communicating encoded information associated therewith to the central computing station 12 for processing and recordation.

Although the type and quantity of encoded information on the product trial media 18 can vary, it is contemplated that each individual product trial media 18 would be encoded with at least the following information:
  a) media identification number;
  b) product identification number;
  c) product name;
  d) product form;
  e) product size;
  f) product quantity;

g) media type;
h) a series of manufacturer I.D. numbers;
i) a date range.

In addition, as illustrated in FIGS. 2A and 2B, each individual product trial media 18 will have printed or embossed thereon certain identifying information such as:
   a) pharmaceutical manufacturer's name;
   b) product name (trade name, generic name);
   c) product form;
   d) product size;
   e) product quantity;
   f) media identification number;
   g) prescriber, patient and pharmacy signature areas;
   h) prescriber and pharmacy approval code areas.

The product trial media 18 can assume various tangible forms. However, in the example illustrated in FIGS. 2A and 2B and discussed herein, the product trial media 18 is in the form of a conventional magnetic card which again is designed to be compatible with a READ-ONLY magnetic reader terminal located at prescriber and pharmacy sites.

It should be appreciated that the product trial media 18 can be used with approved pharmaceuticals that are past the trial stage. Little if any change need be made to the above listed identifying information. However, it may be desirable to include a field that lists the number of refills or remaining validations, if any, that are available to the patient. This field may be decremented each time the prescription is filled. Further, the product media may include fields which designate one of a plurality of participating pharmaceutical products, a quantity and dosage field as needed, or other comparable information that traditionally is located on a prescription sheet. While it is contemplated that one product media could be used for a plurality of pharmaceuticals, it is also contemplated that each pharmaceutical could have its own product media. This may result in excess inventory for the prescriber, but is a viable embodiment of the present invention.

Finally, the system 10 of the present invention includes authorizing media indicated by the numeral 20 that is distributed to participating prescribers and pharmacies. As with the product trial media 18, the authorizing media 20 can be in various tangible forms and in the example illustrated herein, the authorizing media assumes a READ-ONLY magnetic card form that is compatible with the prescriber and pharmacy terminals 14 and 16. Each individual authorizing media specifically identifies a participating prescriber or pharmacy. In the case of prescriber authorizing media, the same would be encoded with various identifying information such as:
   a) the prescriber's name,
   b) prescriber's medical identification number,
   c) prescriber's control I.D. number,
   d) prescriber location identification.

In the case of pharmacy authorizing media, the same would include encoded information specific to and identifying a particular participating pharmacy. The encoded information on such a pharmacy authorizing media would include identifying information such as:
   a) pharmacy name,
   b) name of individual pharmacists associated with the identified pharmacy,
   c) pharmacy control identification number, and
   d) pharmacy location identifier.

Also, as illustrated in FIG. 3A and FIG. 3B, the authorization media 20 includes printed or embossed information thereon such as prescriber or pharmacy I.D. number, pharmacy or prescriber name, card expiration date, and space for the signature of a physician or pharmacist.

As will be discussed in more detail later, the authorizing media 20 is compatible with the prescriber and pharmacy terminals 14 and 16 and consequently, encoded identifying information associated with the individual authorizing media 20 can be reviewed and verified by the central computing station 12 prior to the participating prescribers and pharmacies having access to the central computing station. The authorizing media 20 enables the system and the central computing station 12 in particular to verify that prescribers and pharmacies attempting to enter the system and network are in fact authorized to do so and are in fact authorized participants in the pharmaceutical trial product distribution program of the present invention.

The present invention entails a pharmaceutical trial product distribution method or process where pharmaceutical trial products are actually prescribed by a participating medical doctor or prescriber and not directly delivered to the patient by the prescriber as is conventional practice today. Additionally, normal pharmaceuticals past the trial stage may similarly be so prescribed. Once the pharmaceutical product has been prescribed, the patient then proceeds to a participating pharmacy where the prescription for the trial, sample, or normal pharmaceutical product is filled. Prescriber and pharmacy transactions are all monitored and recorded by the central computing station 12. Periodically, the participating pharmacies are compensated for the trial product and normal products dispensed and the services performed. Compensation would typically include replenishment of dispensed trial or normal product through a wholesaler plus a dispensing fee, all of which is established by recorded transactions within the central database.

It is contemplated that the present system and method for distributing pharmaceutical products would be managed by an independent entity referred to as a program manager and that a number of pharmaceutical manufacturers would join together in a consortium or the like to participate in the pharmaceutical trial product distribution program, all of which would be administered and managed by the program manager. However, it is to be appreciated that the present pharmaceutical trial product distribution system and method can be carried out in other forms including a program administered and managed totally by a single pharmaceutical manufacturer. The same is true if the present invention is used for products past the trial stage.

In developing and implementing the pharmaceutical trial product distribution program or other pharmaceutical product program of the present invention, participating prescribers and pharmacies must be established. In this regard, it is contemplated that the program manager in cooperation with participating pharmaceutical manufacturers or suppliers, sometimes referred to as pharmaceutical members, identify certain prescribers and pharmacies that are authorized to participate in the program. Thereafter, the program manager issues specific authorizing media 20 to each of the prescribers and pharmacies authorized to participate in the program. Note that each authorizing media 20 is specifically encoded to identify a certain prescriber or pharmacy as well as the physical location or locations of that prescriber or pharmacy. In addition to the authorization media 20, prescriber terminals 14 and pharmacy terminals 16 are also delivered to the participating prescribers and pharmacies.

The prescriber and pharmacy terminals 14 and 16 are transaction-based communication units provided with both an EPROM chip and random access memory (RAM) for application operation. Each terminal is electrically powered and adapted to communicate with the central computing station or host 12 through a conventional telephone system. A user keypad having both function keys and a ten-number keypad are incorporated into each terminal. Application, prompt, and approval instructions are communicated through an LED display that forms a part of each terminal.

The EPROM chip of each terminal is provided with a series of data fields that are used in a terminal initialization procedure that is designed to verify that a respective terminal is properly located physically and is under the control of an authorized and participating prescriber or pharmacy. In the way of example, the data fields of the EPROM chip could include: terminal serial number, prescriber or pharmacy identification, location or locations (physical address) for the participating prescriber or pharmacy assigned to that terminal, and location fax and telephone number. In addition, the EPROM chip of each terminal would include a check digit/analog code matrix used in establishing the authenticity of the terminal.

Now, turning to the RAM of the respective terminals, it is appreciated that the capacity of the RAM may vary but it is contemplated a storage capacity of 32K bytes would be sufficient to handle downloaded application programming from the central computing station 12. Data fields for the RAM may include a series of server (central computer station) phone numbers, a check digit/analog code index field, check digit/analog code multiplier-divisor, check digit/analog answerer, check digit/analog code formula, and system date and time.

The above discussion deals generally with the basic prescriber and pharmacy terminals 14 and 16 that are contemplated to be used in carrying out the pharmaceutical trial product distribution method and program of the present invention. Details of the construction and programming of the terminals are not dealt with herein because such is not per se material to the present invention and further, because such terminal designs are well appreciated by those skilled in the art and are in fact commercially available. While various types of terminals may be employed by participating prescribers and pharmacies, it is contemplated that a terminal design of a conventional magnetic card reader would be efficient and cost effective for the present pharmaceutical product distribution program.

Initially, various pharmaceutical members distribute individual product trial media 18 to participating medical doctors or prescribers. This distribution can be carried out by sales representatives of the pharmaceutical members. At the same time, the program manager (administrator of the pharmaceutical trial product distribution program) may distribute both terminals and authorizing media 20 to both participating medical doctors and pharmacies. It is appreciated that prior to the initiation of the program and in fact on an ongoing basis, the database associated with the central computing station 12 is loaded with data corresponding to the distributed product trial media 18 and authorization media 20 as well as data that identifies each individual terminal to be delivered to participating prescribers and pharmacies. Such is important in carrying out the various integrity checks that will form a part of the pharmaceutical trial product distribution program of the present invention. The same is likewise true of prescriptions for products that are outside of the trial stage since these too are subject to strenuous regulatory reporting concerns.

Figure 5:
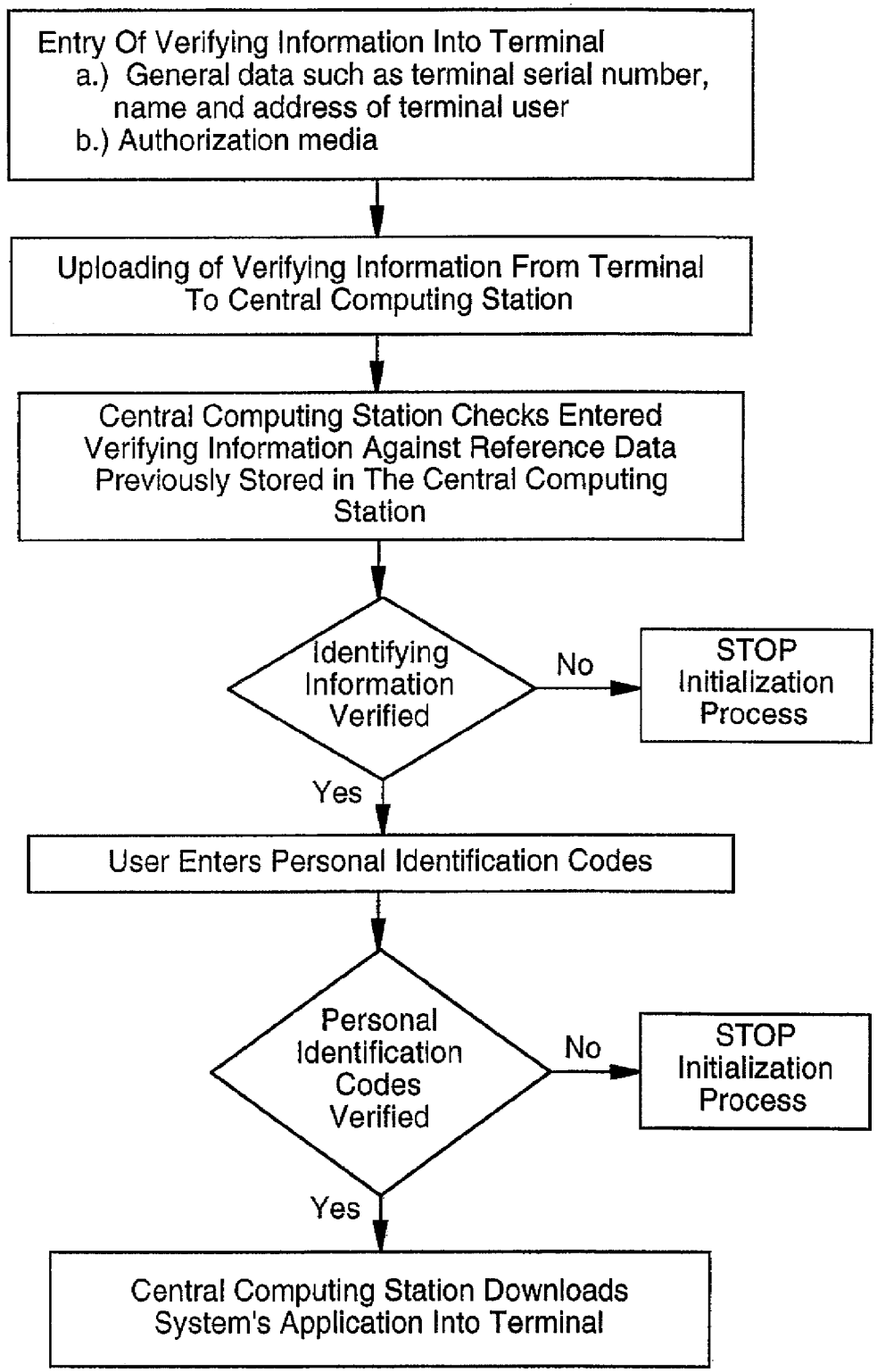
FIG. 5 is a flow chart that depicts the basic steps entailed in terminal initialization, whether it be at the prescriber or pharmacy level.
Figure 6A:
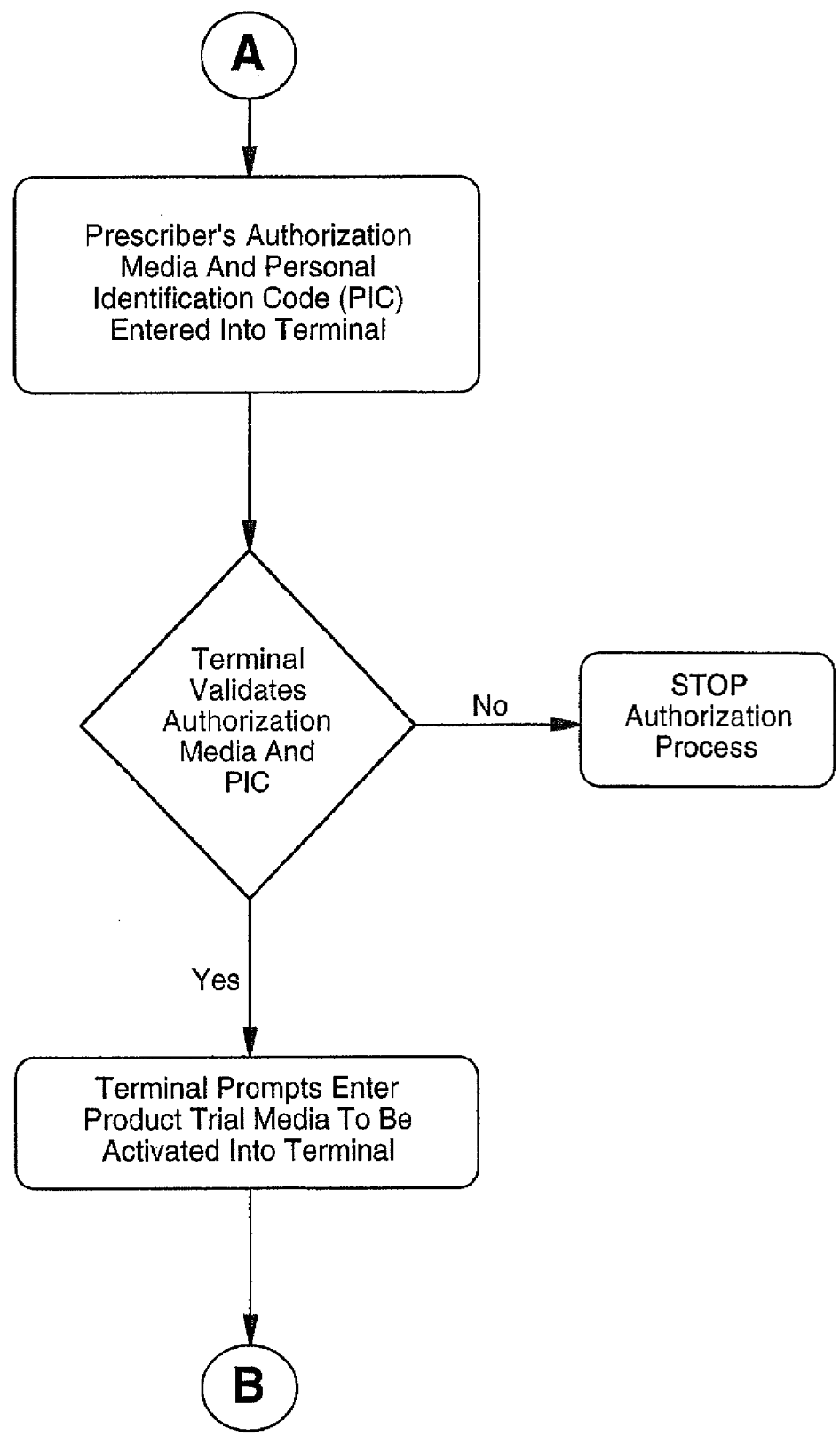
FIGS. 6A-6D depicts a flow chart that shows the basic steps involved in the prescribers activating pharmaceutical trial media.
Figure 6B:
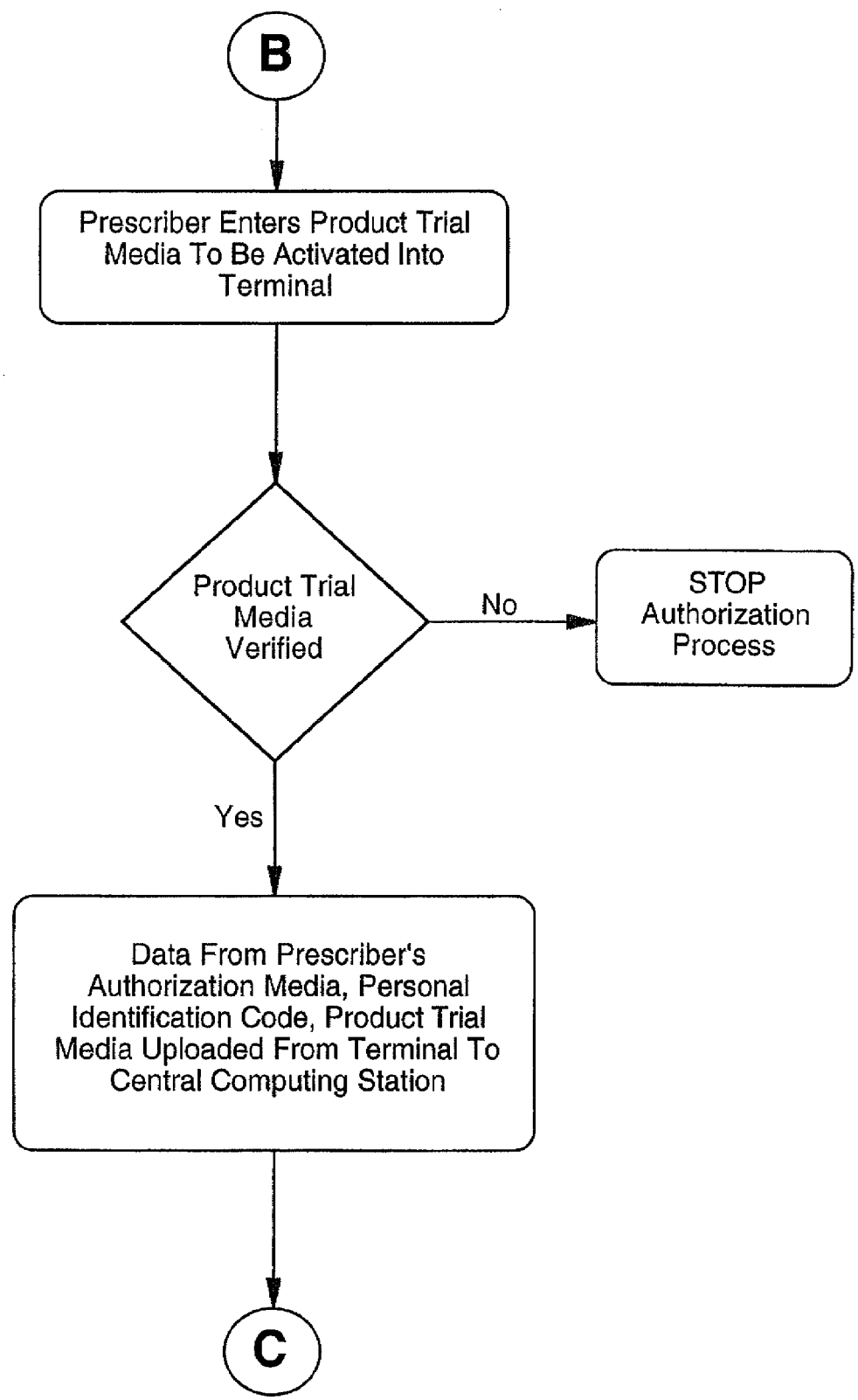
Figure 6C:
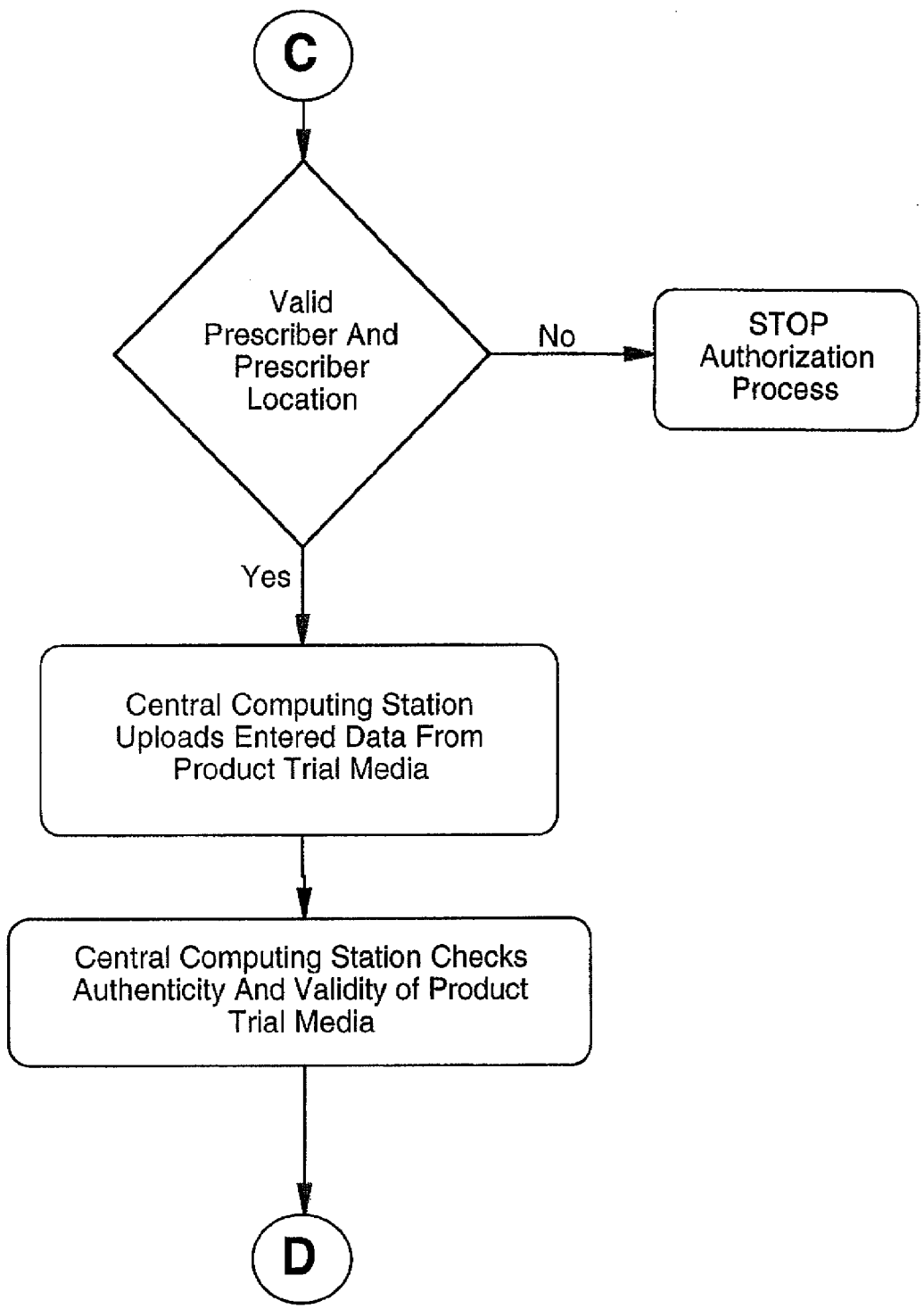
Figure 6D:
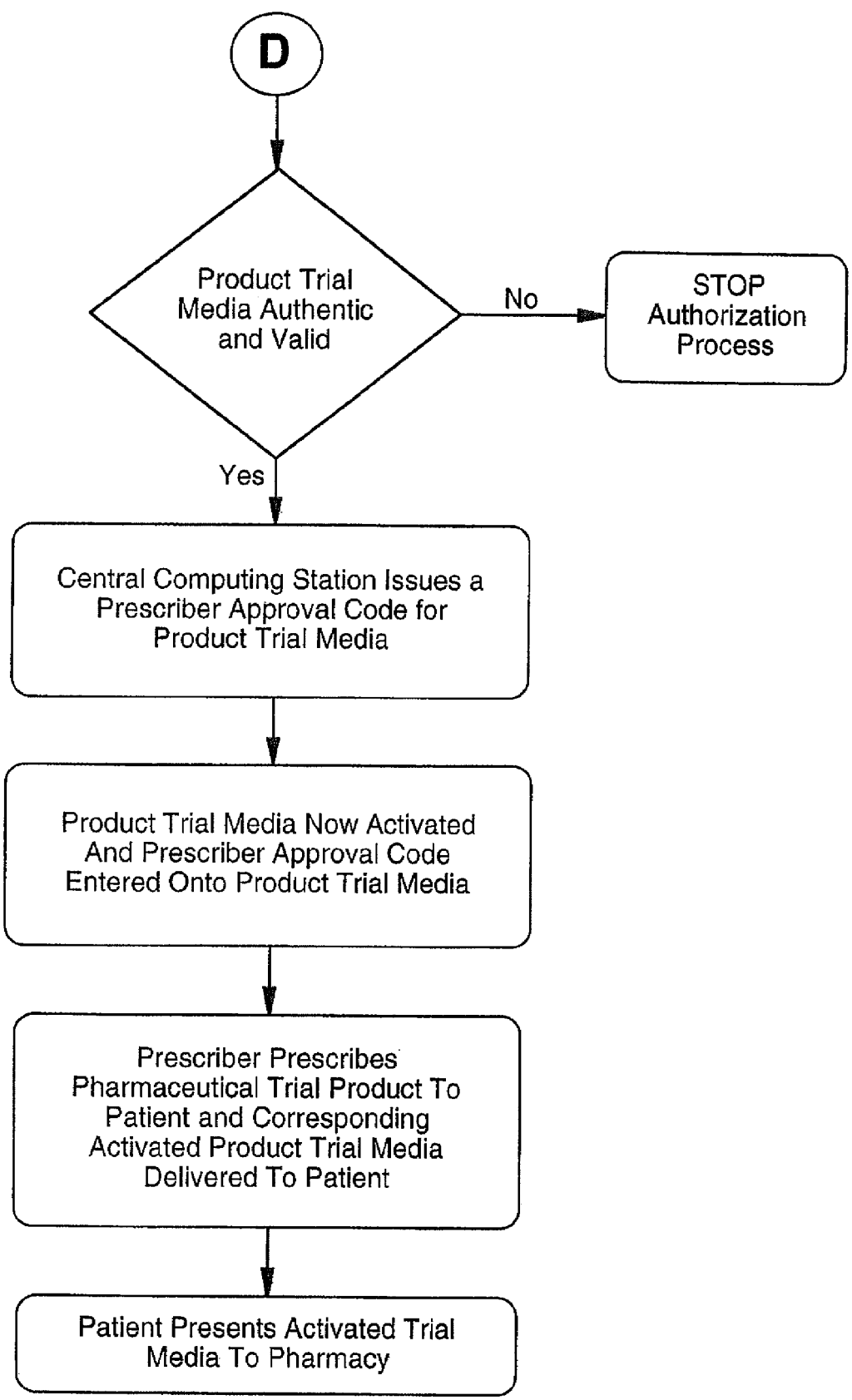
Figure 7A:
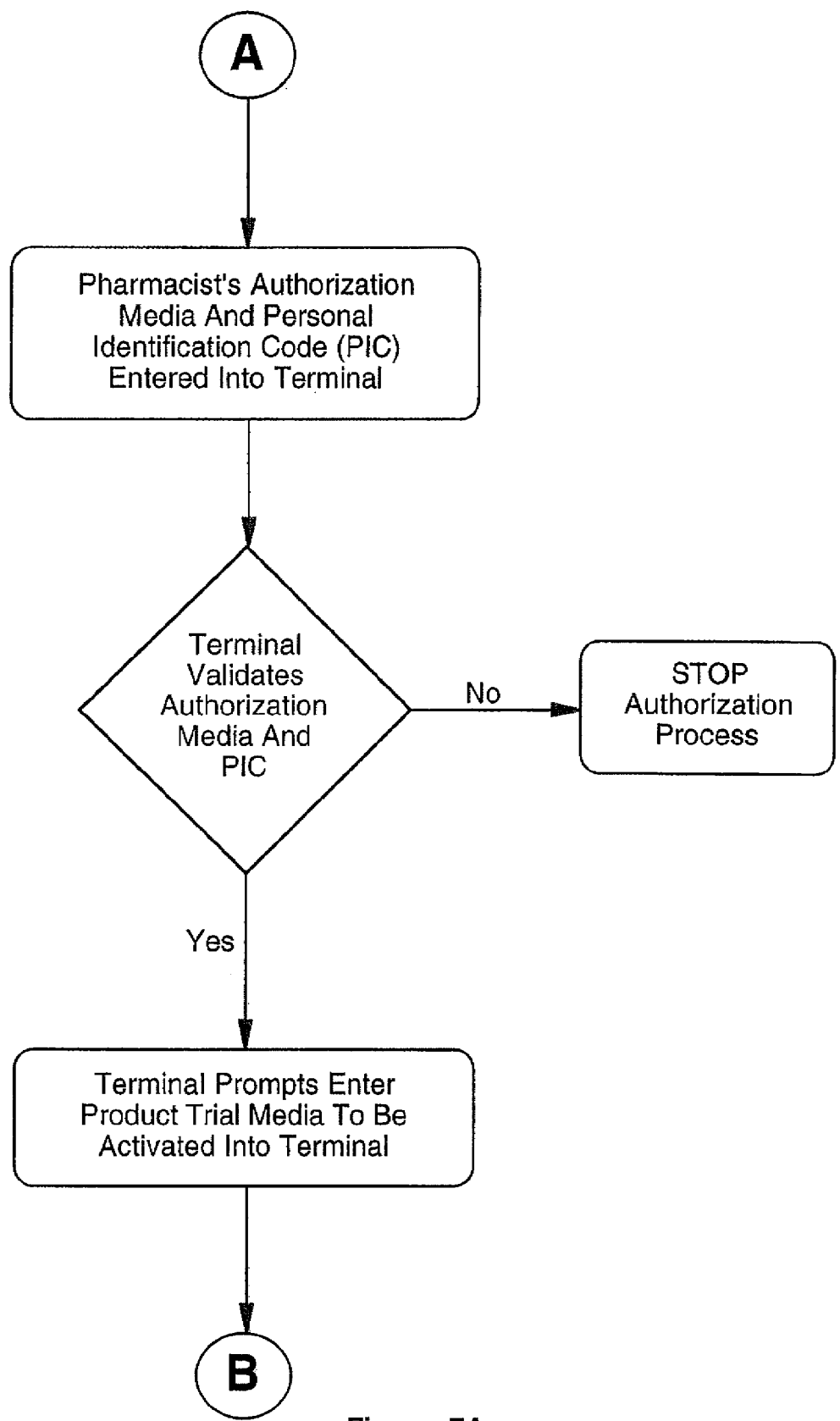
FIGS. 7A-7E depicts a flow chart that shows the basic steps involved in validating activated product trial media and dispensing pharmaceutical trial products in response to the validation of product trial media.
Figure 7B:
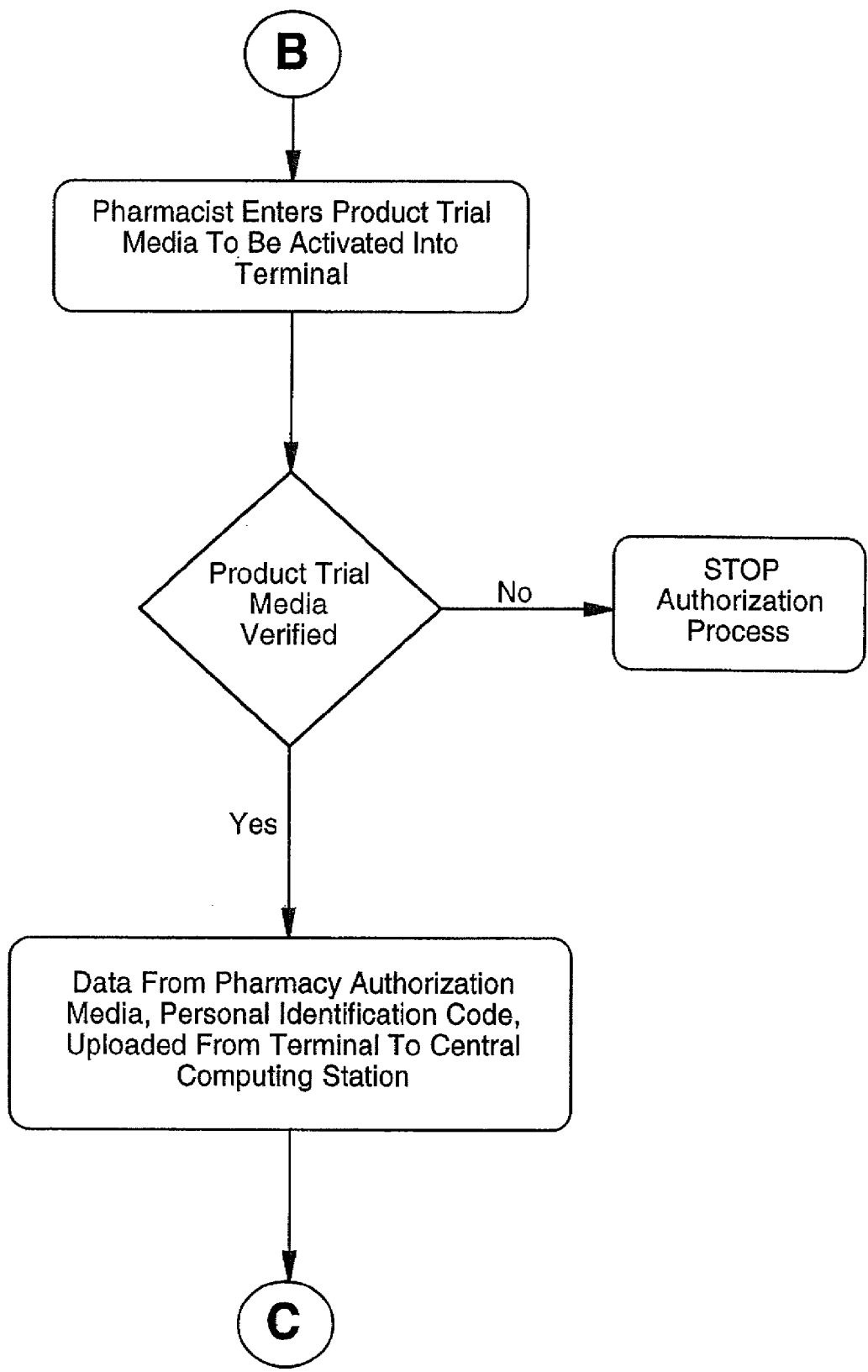
Figure 7C:
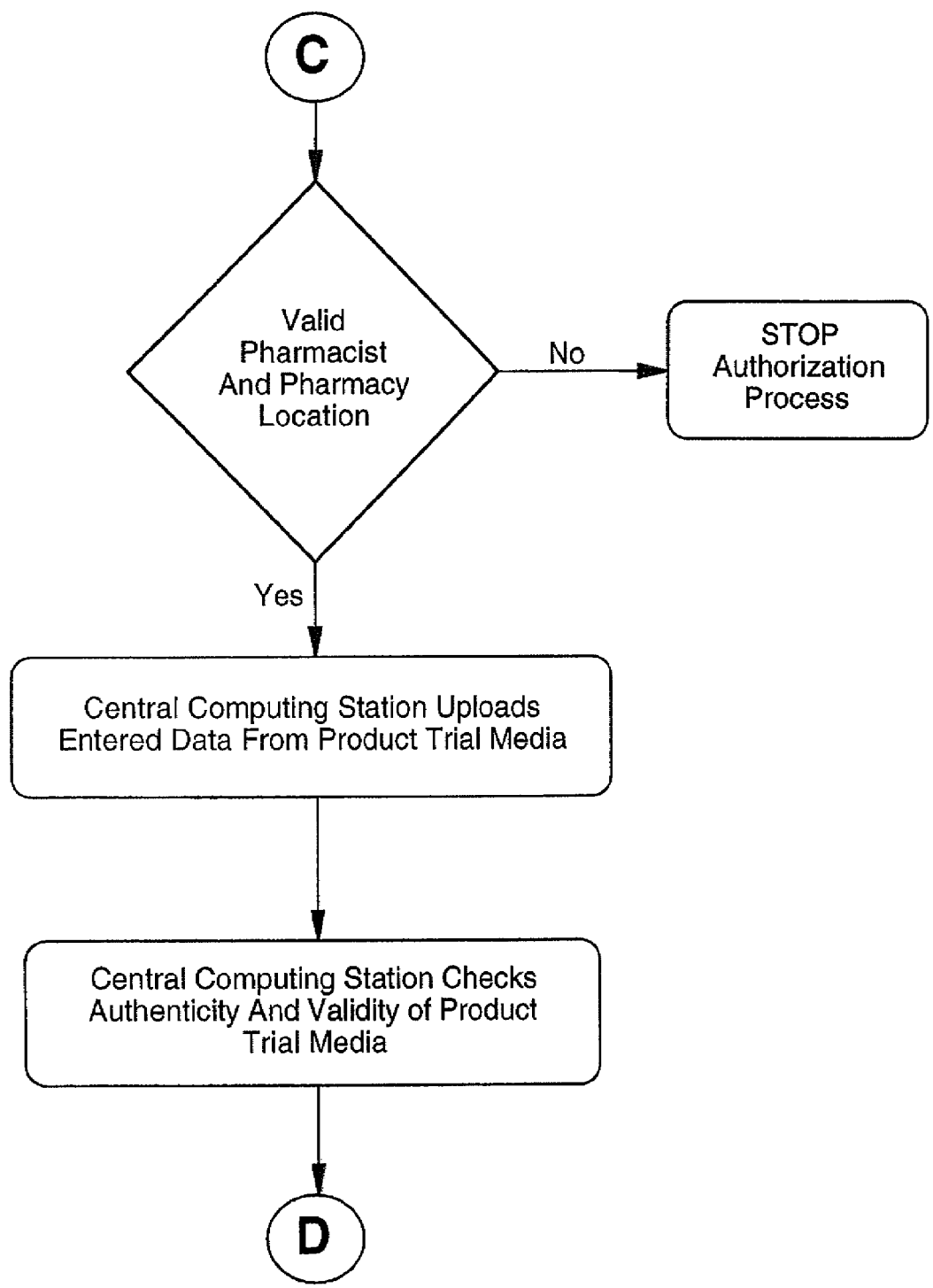
Figure 7D:
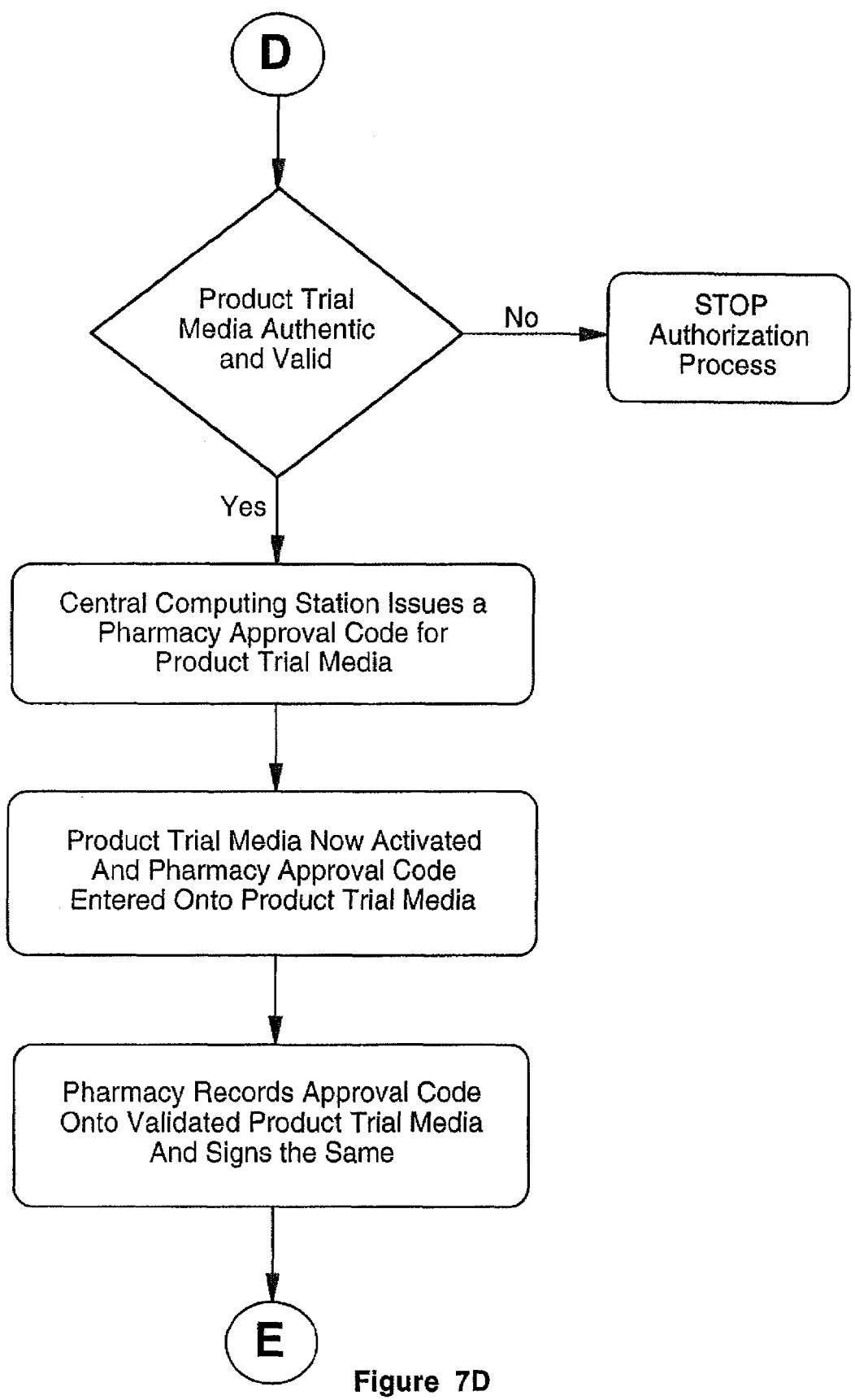
Figure 7E:
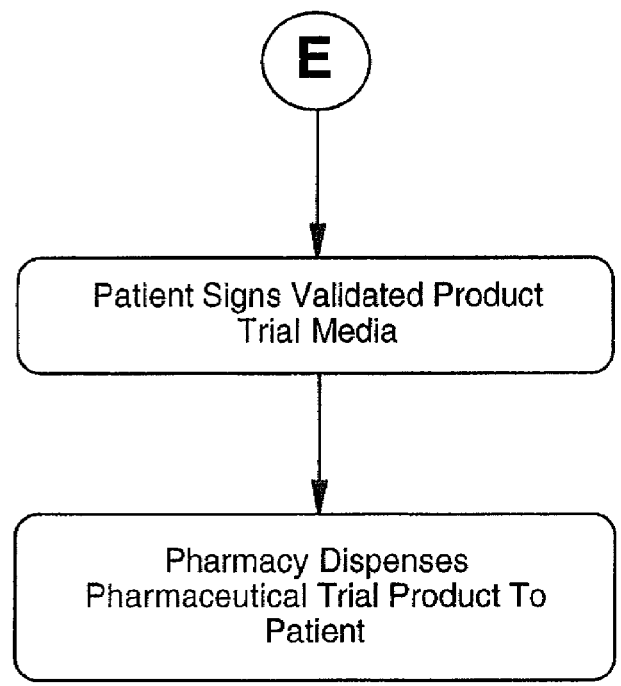

Prior to entering the system and participating in the pharmaceutical distribution program, each participating prescriber and pharmacy must proceed through a terminal initialization process. This terminal initialization process, as illustrated in FIG. 5, is designed to discover and identify unauthorized participants and to generally prevent unauthorized use of the system.

To initialize a terminal, the prescriber or pharmacy connects the terminal to an AC power outlet and a conventional phone line. Once the terminal is placed in an "on" state, the prescriber or pharmacy presses a "setup" function key. The terminal then automatically responds and requests information pertinent to the data fields of the EPROM chip. In the way of examples, the terminal requests the user to input into the issued terminal the terminal serial number, practice name or pharmacy operating from the location of the terminal, the physical address of the location of the terminal, location communication telephone number, location business telephone number and location fax number.

Next, and still as a part of the terminal initialization process, the terminal requests that the prescriber or pharmacy user enter its issued authorization media 20. In the case of a magnetic card media and reader, the prescriber or pharmacy simply swipes its authorization media card 20 through a magnetic card reader and encoded data on the authorization media card 20 is recorded in the RAM of the terminal.

Thereafter, the terminal automatically dials and connects to a terminal initialization service that forms a part of the central computing station 12. The initialization service then uploads all data from the terminal into the database of the central computing station 12 including data recorded on the EPROM chip and information previously encoded on the authorization media 20 and now stored in the RAM of the terminal.

Based on independently entered reference data previously entered into the database of the central computing station, the data uploaded from the terminal during this initialization process can be checked against the reference data already stored in the database of the central computing station. At this point, the central computing station can verify whether a certain serial number terminal is properly coupled with a certain physical location and with a certain prescriber or pharmacy. If all relevant data uploaded from the terminal does not correspond to the reference data then the initialization process is failed and access to the system and program is denied.

In the specific initialization method being discussed herein, the above does not complete the total initialization process. After passing the above, the individual prescriber or pharmacy is requested to enter a personal identification code, commonly referred to as a PIN. The personal identification code is furnished confidentially to the participating prescribers and pharmacies through the program manager and can be permanent or temporary. If temporary, the user will be subsequently requested to enter a personally devised code which becomes the user's permanent identification or PIN code. In any event, after the central computing station has requested entry of the user's personal identification code, the participating prescriber or pharmacy then enters the personal identification code into the system database and the central computing station then verifies the personal identification code and cross-checks the same with respect to uploaded terminal data, that is, data found on the EPROM chip and the terminal's RAM. If the personal identification code entered is determined to be an invalid personal identification code for any reason, the prescriber or pharmacy is denied access to the system. On the other hand, if the personal identification code is deemed to be valid then the central computing station indicates on the terminal's display "downloading application." At this time, the system's application is then downloaded into the terminal's RAM storage. Thereafter, the terminal displays "download complete" and this completes the terminal initialization process. The initialized terminal is then ready to be used on a periodic basis in the pharmaceutical trial distribution program of the present invention. Note that this same initialization process is carried out for both participating prescribers and pharmacies.

The product trial media 18 or other pharmaceutical product media delivered to the participating prescribers arrive in an unactivated state. That is, the product media in an unactivated state cannot be validated by a participating pharmacy and accordingly, pharmaceutical product identified by that media cannot be dispensed. In essence, the pharmaceutical product media are blank prescription forms and have not been filled in by the prescriber or "validated" according to the present invention. In the method of distributing pharmaceutical product of the present invention, the participating prescribers actually activate the product media through a procedure where the product media is communicatively linked with the central computing station or host 12 via a prescriber's terminal. See FIGS. 6A-6D which show a flow chart that depicts the basic steps involved in the activation process. However, before any unactivated product media can be activated by a prescriber, the prescriber must establish authorization. This can be carried out in a variety ways. In one embodiment of the present invention, activation of product media 18 is conditioned first upon the prescriber evidencing a valid authorization media. This is accomplished by the prescriber's terminal reading the prescriber's authorization media 20. Encoded information associated with the prescriber's authorization media 20 is recorded within the RAM of the prescriber's terminal. In particular, the terminal records the prescriber's identification number associated with the prescriber's authorization media 20. At that point, the terminal requests the prescriber to enter the prescriber's personal identification code. Next, the terminal requests the prescriber to enter the quantity (number) of pharmaceutical media that the prescriber desires to activate. Thereafter, the prescriber enters into the keyboard of the prescriber terminal the numeric quantity of product media 18 to be activated by the system. The prescriber terminal then prompts the prescriber to communicatively link the product media to be activated with the prescriber's terminal. In cases where the product trial media 18 assumes the form of magnetic cards for example, the prescriber simply swipes the product trial cards to be activated through a card reader-type terminal. One by one, the prescriber swipes the product trial media to be authorized through the prescriber's terminal. This is also true of other product media.

As each product trial media is read by the prescriber's terminal, an authenticity check is made by the terminal. Specifically, the prescriber's terminal authenticates each product trial media read into the terminal. While various forms of authentication can be performed, in the present method, authenticity is established by the prescriber's terminal checking the product trial media I.D. and verifying that a valid answer results from the various check digit/analog code fields stored in the terminal. If the product trial media is deemed authentic, then the prescriber's unit then displays "product trial media valid." If the prescriber terminal determines that the product trial media is not valid, the terminal indicates such and the product trial media is not activated.

Once the prescriber has completed the activation of a certain number of product trial media the prescriber terminal dials a central computing station 12. At this point, the prescriber terminal uploads stored information corresponding to the prescriber authorization media and the prescriber identification code to the central computing station 12. The central computing station 12 validates the prescriber authorization media and the personal identification code. Once this validation has been established the central computing station uploads all of the product trial media information previously read into the prescriber's terminal during the present activation procedure. It is at this time that the central computing station 12 approves the "activation" of the entered product trial media and issues a specific approval code to the prescriber. The prescriber then records the prescriber approval code onto the face of the respective individual product trial media just activated. Once certain product trial media 18 has been activated, the central computing station 12 denotes in its associated database that certain product trial media 18 has been activated, the activation date, and the identity of the prescriber activating the product trial media. The prescriber then appropriately stores the activated product trial media 18.

The same procedure is likewise applicable to more traditional prescriptions. In such a case, the prescriber receives a prescription media comparable to the product trial media 18 and activates it substantially identically to the technique described with reference to the product trial media 18. Additionally, the prescriber may indicate a number of refills to which the patient is entitled. Further, the prescriber may be required to enter the particular pharmaceutical that is being prescribed, quantity, and other comparable information. If each product media represents a different pharmaceutical, such may not be required.

To dispense the pharmaceutical trial product represented by the activated product trial media, or the prescription drug represented by the prescription media the prescriber signs the product trial media or alternative media and delivers the same to a participating patient. The patient in turn presents the activated media to a participating pharmacy for the purpose of filling the prescription of the prescriber.

Prior to actually filling the pharmaceutical prescription, the participating pharmacy, like the prescriber, must establish authorization. First, like the prescriber, the pharmacy terminal is subjected to the initialization test discussed above. This basically establishes that the issued terminal to the participating pharmacy is in fact the correct terminal, is properly physically located, and is associated with the assigned pharmacy. Again, this initialization procedure, as discussed above, is not contemplated to be a daily procedure but is only a basic initialization step for the participant utilizing the terminal and the system.

However, before the pharmacy can fill the prescription of any presented media 18, the media must be subjected to a "validation" procedure. The "validation" procedure is basically illustrated in FIGS. 7A-7E. Essentially, this validation procedure establishes that the presented media 18 is authentic, still within an acceptable date range, has been activated by a prescriber, and has not previously been validated, or if previously validated, still has valid refills available. Once validation is established for any presented media, then the participating pharmacy can issue the prescriptive pharmaceutical product to the patient.

Details of the validation process will not be dealt with here in great detail because pharmaceutical "validation" of media parallels prescriber "activation" of the media just described. That is, "validation" by the participating pharmacy entails steps and procedures that are similar in function and result as the steps and procedures engaged in by the prescriber in activating certain media. But briefly, the validation step entails the participating pharmacy establishing authorization. This can be carried out in a variety of ways. However, in the process contemplated herein, the participating pharmacy would communicatively connect its authorization media 20 with the pharmacy terminal and after establishing a valid authorization media the participating pharmacy would enter its personal identification code. Thereafter, the terminal prompts the pharmacy to read the presented media 18 into the terminal. As an individual media is read into the pharmacist's terminal, the terminal first checks for complete authenticity of the presented media 18. Like with the prescriber, the identification of the media is checked, the date range of the media is checked and the terminal seeks a valid answer from the check digit/analog code fields. If authenticity is not established, it follows that the participating pharmacy cannot dispense corresponding pharmaceutical product. However, if authenticity is established then the pharmacies' terminal dials the central computing station and data and information from the pharmacies' authorization media and personal identification is uploaded to the database of the central computing station 12. The central computing station establishes that the uploaded information is valid and then information from the pharmacies' terminal related to the presented media 18 is uploaded to the central computing station. Assuming full validation, the central computing station issues a pharmacy approval code and the pharmacy records that approval code on the actual presented media 18. In addition, both the pharmacy and the patient sign the now validated media 18. Once validation is established the pharmacy then dispenses pharmaceutical product authorized by that valid media and permanently stores the validated media. At the same time, the central computing station 12 records the full validation data within its database by showing that a particular media 18 has been validated, the date of such validation, and the identity of the pharmacy validating the same.

Obviously, the database associated with the central computing station 12 will possess a full record of all transactions of the program including activations and validations. Importantly, the recorded transactions reveal the dispensing activities of each participating pharmacy. This serves as a basis for replenishing to the participating pharmacy pharmaceutical products dispensed in the present program and for the payment of dispensing these to the participating pharmacies. Typically, the pharmaceutical to be replenished can be replenished through wholesalers that serve the participating pharmacies.

A wealth of data can be discerned from the central computing database. For particular pharmaceutical members, data representing the identity of product and the quantity of a particular product prescribed and dispensed over a selected period of time is obviously readily available. More detailed data and records representing the specific activities of particular prescribers or pharmacies are also available. In the end, a wide variety of reports can be generated from the database. These reports can be so extensive and so detailed that the participating pharmaceutical members can study and evaluate "cause and effect" based on the recorded data.

In summary, the present method of tracking and managing the dispensing of pharmaceutical products centers around the utilization of a group of authorized prescribers and pharmacies and a centralized computing station that is specifically linked to the participating prescribers and pharmacies. Media capable of being exchanged at a pharmacy for pharmaceutical product are delivered in an unactivated state to participating prescribers. After establishing authorization, the prescriber through a remote terminal and the central computing station "activates" certain product media. Once activated, the product media is capable of being prescribed or exchanged for a pharmaceutical product at a participating pharmacy site. The activated pharmaceutical media 18 is then delivered to a patient and the patient in turn presents the same to a participating pharmacy. The pharmacy must establish authorization to participate in the system and thereafter the presented activated media is authenticated by the central computing station and is deemed valid. Next, the pharmacy dispenses the pharmaceutical product identified by that media. Thereafter, an audit and accounting function is performed based on the database associated with the central computing station. Accordingly, participating pharmacies can be compensated for the actual dispensed pharmaceutical product and for dispensing services performed.

The method and program has been described as being carried out by utilizing magnetic cards and magnetic terminal readers. However, it is appreciated that other media forms and various types of terminals or communication methods could be utilized to carry out the basic method of tracking and managing the distribution of pharmaceutical trial products.

Figure 8:
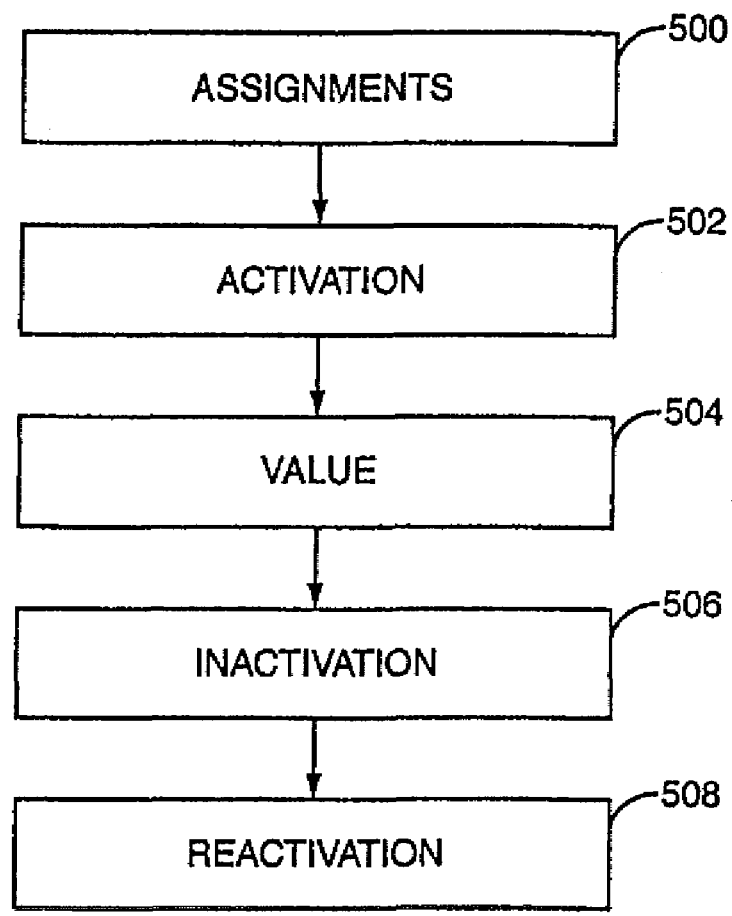
FIG. 8 illustrates a first flow chart showing an overview of an alternate embodiment of the present invention.

The system and method described hereafter relates to the disclosures found in the parent applications. In particular, the methods and systems disclosed below are designed to help maximize profits, gather and collect important marketing data and information, and reward consumers and the public in the process. To this end, the manner of activation of the media 18, or other conditions or criteria, may determine, in part, the value of the media. Thus, the value of the media 18 may vary. For the purposes of this disclosure "the value of the media" can relate to any value and may, for example, be in the form of goods, services, discounts for goods or services, etc. The media 18 can also be utilized to promote and deliver services. As will be discussed below, when used in a service context, the value of the services that are delivered via the media can also vary. Further, where or when the media is redeemed may determine, in part, the value of the media. Further still, the media may provide different values depending on how the media is activated or reactivated. By varying the value of the media 18, different prescribers and pharmacies, in a pharmaceutical context, may be preferentially treated in such a manner that it builds loyalty to a particular pharmaceutical company or distribution channel. The present invention has been described in the context of pharmaceutical and medical products. However, it should be appreciated that the basic invention described herein can be utilized to promote and advertise any good or service. Consequently, the invention can be described in terms of not only prescribers and pharmacies, but can be described in terms of providers of goods, products and services as well as in terms of those individuals and businesses that play a part in the manufacture, distribution, and sale of such products or services. An overview of the process is illustrated in FIG. 8.

Initially, the process assigns media units to location, companies, people, groups, or the like (block 500). This may be done by assigning batches of media to a particular assignee or by assigning a single medium to a particular assignee. The media are subsequently activated (block 502). This may be a fixed activation or a variable activation as is explained in greater detail below. The media assumes a value (block 504). Financial rules are put in place to govern the use of the media. This may be a fixed value, wherein the media only has one value and assumes this fixed value upon activation as described in the parent applications and above; or may be a variable value, wherein the media assumes different values based on predetermined business rules, selected criteria, or other selected circumstances, conditions, or occurrences. For example, the value may be based on a patient's co-payment, activity based rewards, location, date and time of activation, how the media was activated, and/or whether the media is being concurrently used to purchase one or more products. The media are inactivated (block 506) after use or a predetermined time. That is, the value of the media diminishes or is purged. Optionally, the media may be reactivated (block 508) and assume value again. In the way of an example, the media may remain activated for a variable time, depending on certain criteria, circumstances, etc. Also, in terms of activation, as will be explained herein, there are various forms of activation. For example, the system and method of the present invention can be utilized in a referral program where the holder obtains one medium and four referral media. The one medium is automatically activated when the four referral media are activated.

Turning now to the details of some of the steps enumerated above, block 502 refers to media activation and allows for the possibility of fixed or variable activation. For a medium that has a fixed activation technique, a single, predetermined technique or act activates the medium. Exemplary activation techniques comprise time elapsed, user activity, or geographic location. User activity may be a phone call to a central database to activate the medium, a web access to activate the medium, filling out a business return card and returning the same to a selected address, taking the medium to a pharmacy, a referral by a medical provider, or the like. A geographic activation technique may be tied to a location sensor that determines when the media is within a certain predetermined geographic area and activates the media upon reaching that geographic area. Alternatively, media activation within a predetermined geographical area may be determined through any number of conventional means. Where the prescriber's terminal or pharmacy terminals are used, they may provide the desired geographical information. Alternatively, block 502 may also comprise a variably activated media, in which a person or persons activating the media, has a choice among at least two of the activation techniques available with which to activate the media. Different media may have different pluralities of techniques available with which to activate the media.

The inactivation step (block 506) may be fixed or variable as well. In the case of a fixed inactivation, the media has one inactivation option—for example, the media becomes inactive upon use. For variable inactivation media, the media may be inactivated based on some predetermined rules such as time elapsed, failure to refill a prescription, failure to respond to a communication, geography, or the like. If any of these criteria are met, the media may be inactivated.

The reactivation step (block 508) is an optional step wherein there may be no reactivation options—once the media is used. Alternatively, there may be a fixed reactivation process. Thus, the media may only reactivate according to one predetermined criterion, such as time elapsed, user activity, geography, or the like. These can be identical to the criteria recited above with respect to the initial activation criteria. Likewise, there may be a variable reactivation process, wherein the media may be reactivated through one of a plurality of different techniques. Again, the list of techniques is similar to the list that can trigger initial activation.

Figure 9:
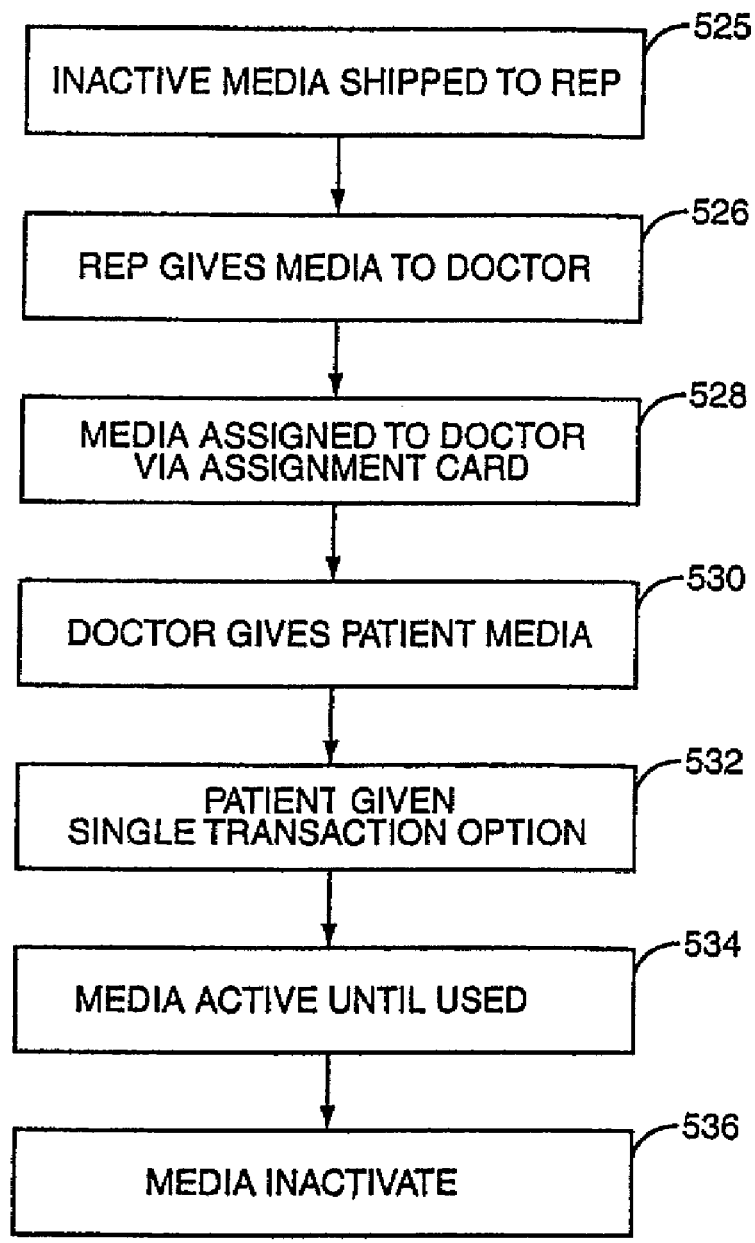
FIGS. 9-13 illustrate exemplary alternate embodiments of the process of the variable valued media of the present invention.
Figure 10:
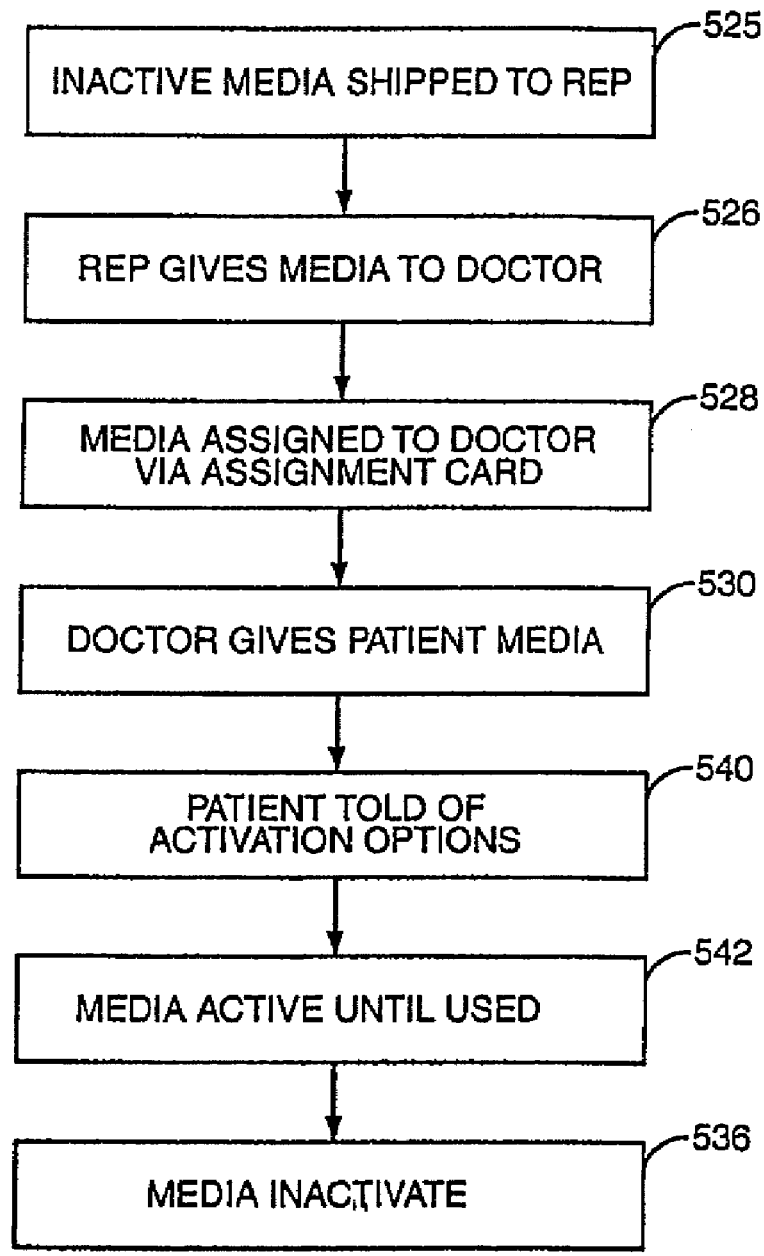

To assist in understanding the media activation and reactivation processes, FIGS. 9 and 10 illustrate broad views of media activation for both fixed media and variable media respectively.

FIG. 9 illustrates a flow chart of fixed activation media. Specifically, the media starts out inactive and is shipped to a sales representative (rep) (block 525). The rep gives the media to approved medical personnel such as a doctor (block 526). The media is assigned to the doctor via an assignment card (block 528). The doctor distributes the media (block 530) to one or more patients, who may only exercise a single predetermined activation method in order to activate the medium (block 532). The media remains active until use at a particular pharmacy (block 534). After use, the media goes inactive (block 536). In this manner, certain doctors and pharmacies are rewarded for their participation in the program. Likewise, favorable distribution arrangements and the like may also be made if needed or desired.

FIG. 10 illustrates a flow chart of variable activation media. Specifically, the media starts out inactive and is shipped to a rep (block 525). The rep gives the media to approved medical personnel such as a doctor (block 526). The media is assigned to the doctor via an assignment card (block 528). The media are given to a patient by the doctor (block 530). The patient is told that they have multiple activation transaction options, and that the media will assume different values depending on how the media is activated (block 540). In some cases, the various activation options will be set forth on the media itself. The media remains active until used by the patient (block 542). After use, the media goes inactive (block 536). FIGS. 9 and 10 illustrate the media 18 being distributed to doctors or prescribers and ultimately redeemed through pharmacies. Those people skilled in the art will appreciate that pharmaceutical goods are simply one type of goods that can be promoted or delivered through the method and system of the present invention.

Figure 14:
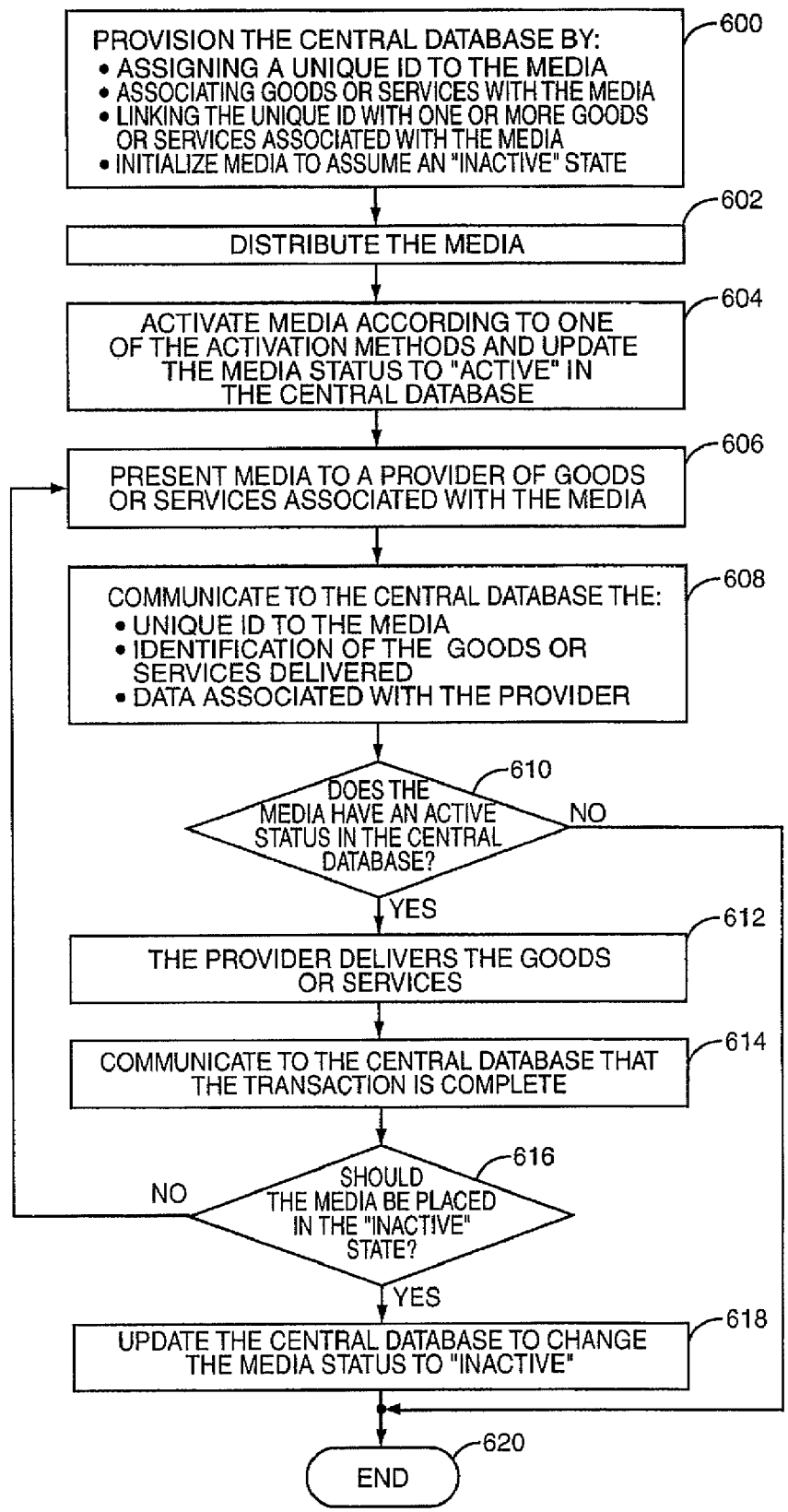
FIG. 14 is a flow chart illustrating media used in the exchange for goods or services and how the media moves between active and inactive states.

Referring now to FIG. 14, one exemplary embodiment of the invention further illustrates the media activation process. In this embodiment, provisioning the central database with data (block 600) identifies the media and initializes the media to an inactive state. Provisioning the central database information may include, among other provisions, the following:

a) assigning a unique ID to each medium of the media;
   b) associating goods or services with each medium;
   c) linking the unique ID of each medium with one or more goods or services associated with the medium; and
   d) initializing the medium to assume the inactive state.

Once the central database has been provisioned, the media is then distributed (block 602) to the end users. In past examples, a pharmaceutical context illustrated representatives distributing the media to a number of doctors who, in turn, distributed them to patients. Those skilled in the art will readily appreciate, however, that end users, sometimes referred to as individuals or holders, are anyone presenting the media to a provider for any goods or services.

Media activation (block 604) usually occurs prior to the redemption for goods and services. In some cases, the media can only be activated by a single method. In other cases, variable activation methods may be available, such as the via the World Wide Web, calling a toll-free 8xx number, responding with a business reply card, or communicating with the central database through a terminal, such as a magnetic card reader. The benefit of the variable activation is that the end user, or whoever activates the media, may choose to exercise any number of activation methods.

Upon the reception of an activation request, the central database updates the media status to active (block 604). It should be noted that, prior to complying with the activation request, the central database may execute an internal process designed to authenticate and approve the media for activation. This internal process may check the data received with respect to the activation request against the data already provisioned in the central database, including such information as the medium identification, the current medium status, and the location of medium activation. Thus, invalid activation requests are not honored and, optionally, alarms may be configured to alert specific operators to the existence of possible fraudulent activity. Valid requests, however, are honored and result in the activation of the medium. Once activated, the medium is ready for presentment, usually to a provider for redemption of goods or services (block 606).

The provider, upon presentment of the medium, communicates the data associated with the developing transaction (block 608) to the central database. This communication supplies the central database processes with the parameters required for validation purposes, which may closely parallel the validation performed during the activation stage. For instance, the media status currently recorded in the central database is checked (block 610). Therefore, proposed transactions using inactive media result in a denial of the transaction, while those transactions using active media are approved, thus authorize the provider to deliver the goods or services (block 612) to the end user. The provider then communicates the completion of the transaction to the central database (block 614), causing the central database to record the nature of the transaction. As discussed herein, all goods or services may not be redeemed at once, thereby defining a residual value attached to the medium. In most cases, where a residual value exists, the central database will determine that the medium should remain active (block 616), facilitating subsequent presentment to a provider for the redemption of additional goods or services (block 606). Those media with no residual value are inactivated (block 618), of course, by the central database and the process ends (block 620).

Figure 11:
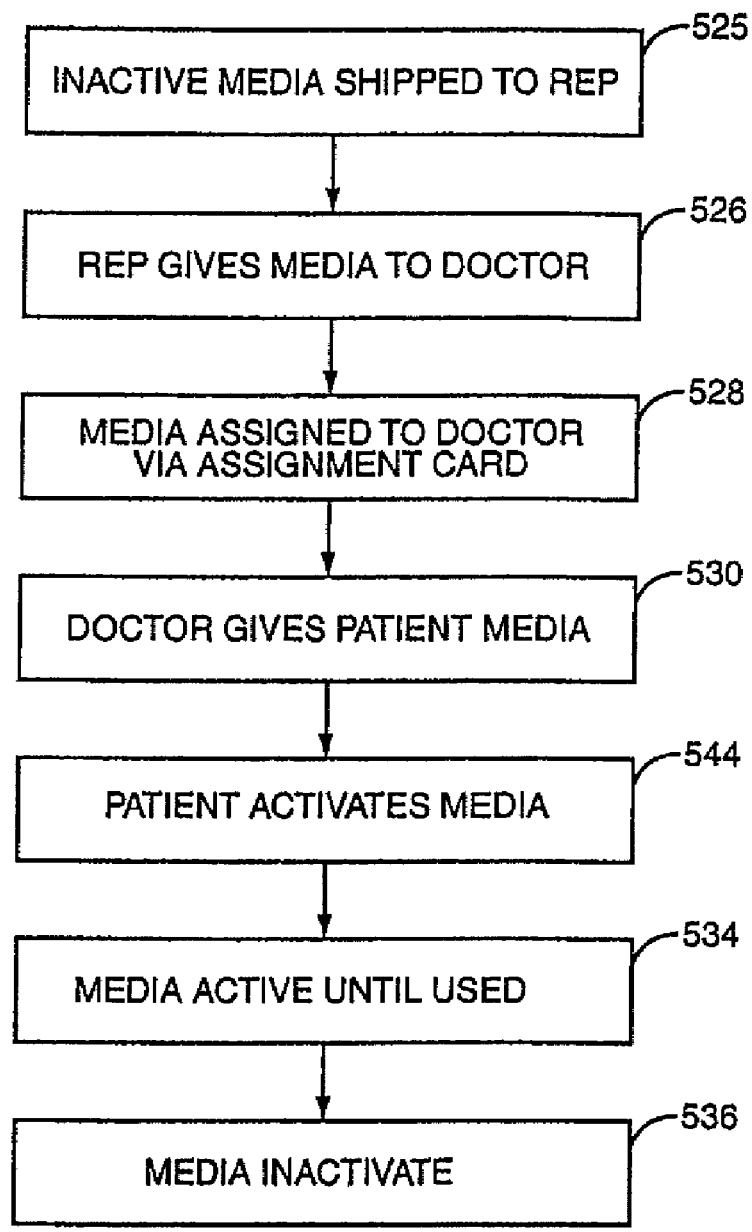

FIG. 11 illustrates a flow chart of fixed value media. Specifically, the media starts out inactive and is shipped to a rep (block 525). The rep gives the media to approved medical personnel such as a doctor (block 526). The media are assigned to the doctor via an assignment card (block 528). Assignment data should be communicated to the central database where the assignment is recorded. In particular, the recordation of an assignment essentially links the media with a prescriber in this case. Various means can be employed to communicate the assignment data and information to the database. For example, a magnetic card reader can be provided at the prescriber's office and communicatively connected to the database. Once the assignment function has been completed, the medium is given to one or more patients by the doctor (block 530). The patient activates the media via any of the approved techniques such as via the web, dialing an 8xx number, responding with a business reply card or the like (block 544). Regardless of how it is activated, the media has a fixed value. The media remains active until use at a pharmacy (block 534) and then goes inactive (block 536).

Figure 12:
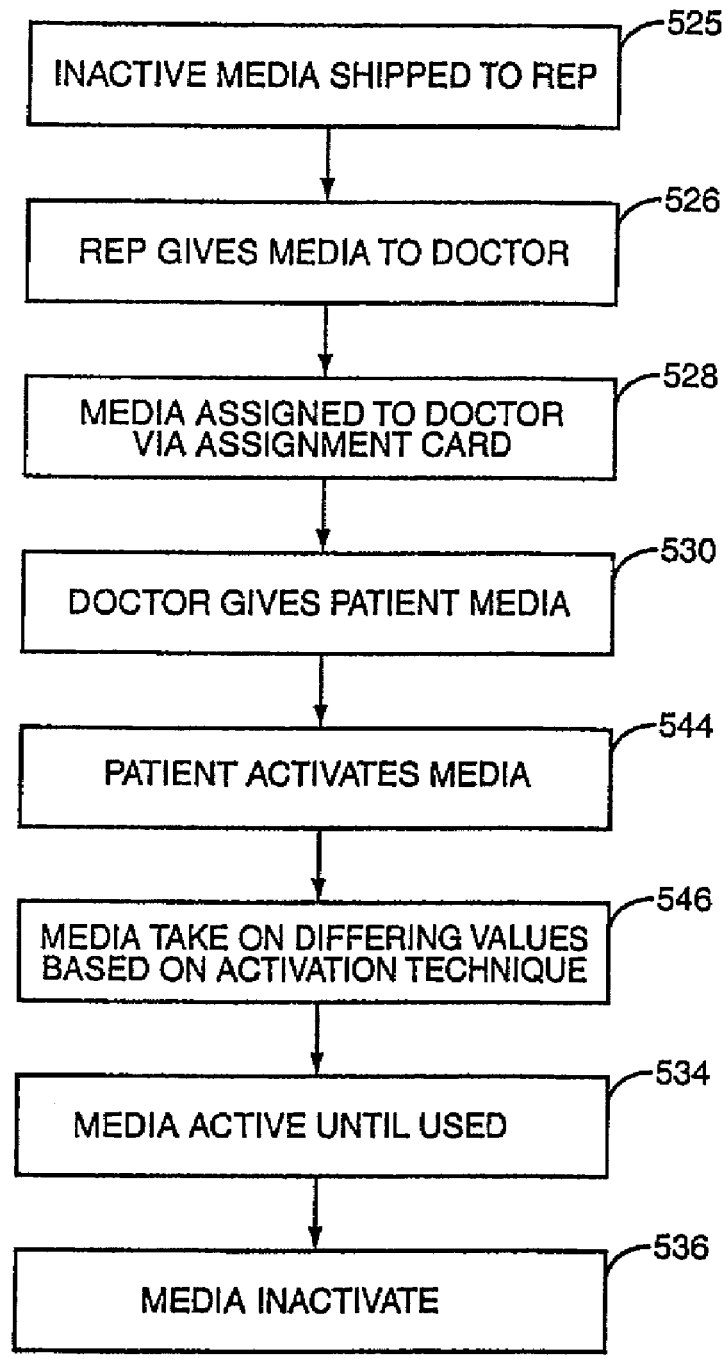

FIG. 12 illustrates a flow chart for variable value media. Specifically, the media starts out inactive and is shipped to a rep (block 525). The rep gives the media to approved medical personnel such as a doctor (block 526). The media are assigned to the doctor via an assignment card (block 528). The media is given to a patient by the doctor (block 530). The patient activates the media via any of the approved techniques such as via the web, dialing an 8xx number, responding with a business reply card, or the like (block 544). The media takes on a different value based the predetermined business rules (block 546). For example, if activated through the business reply card, one sample may be given to the patient; if activated through an 8xx number, two samples may be given to the patient; and if activated through the web, three samples may be given to the patient. The media remains active until use at a pharmacy (block 534) where the patient is provided with a number of samples according to the value assigned at activation, and then goes inactive (block 536).

Figure 15A:
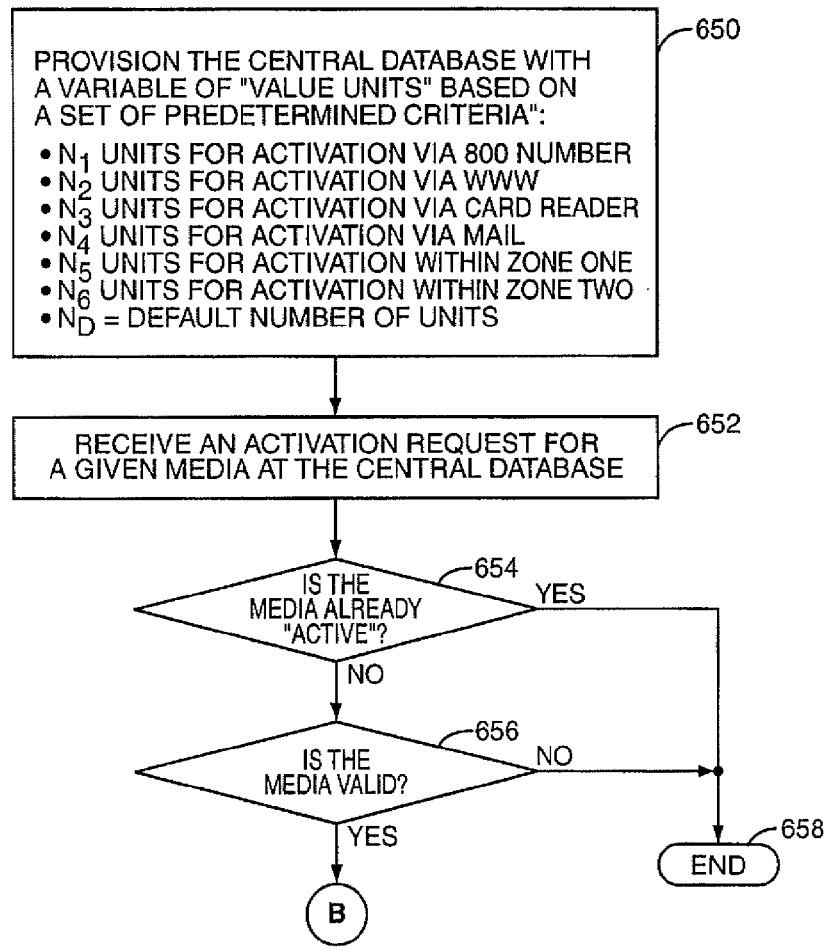
FIGS. 15A-15C depict a flow chart showing how the media can assume variable values.
Figure 15B:
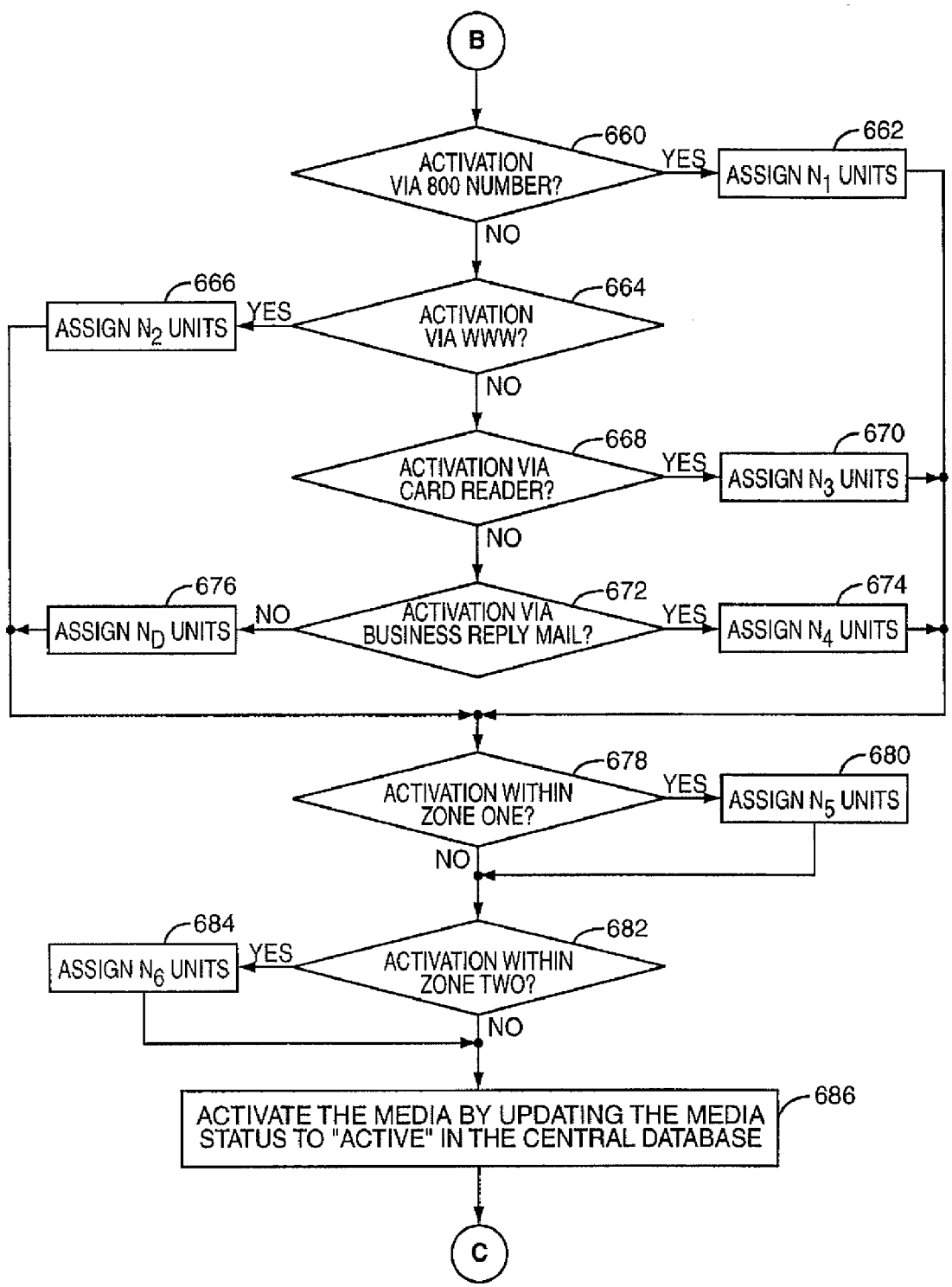
Figure 15C:
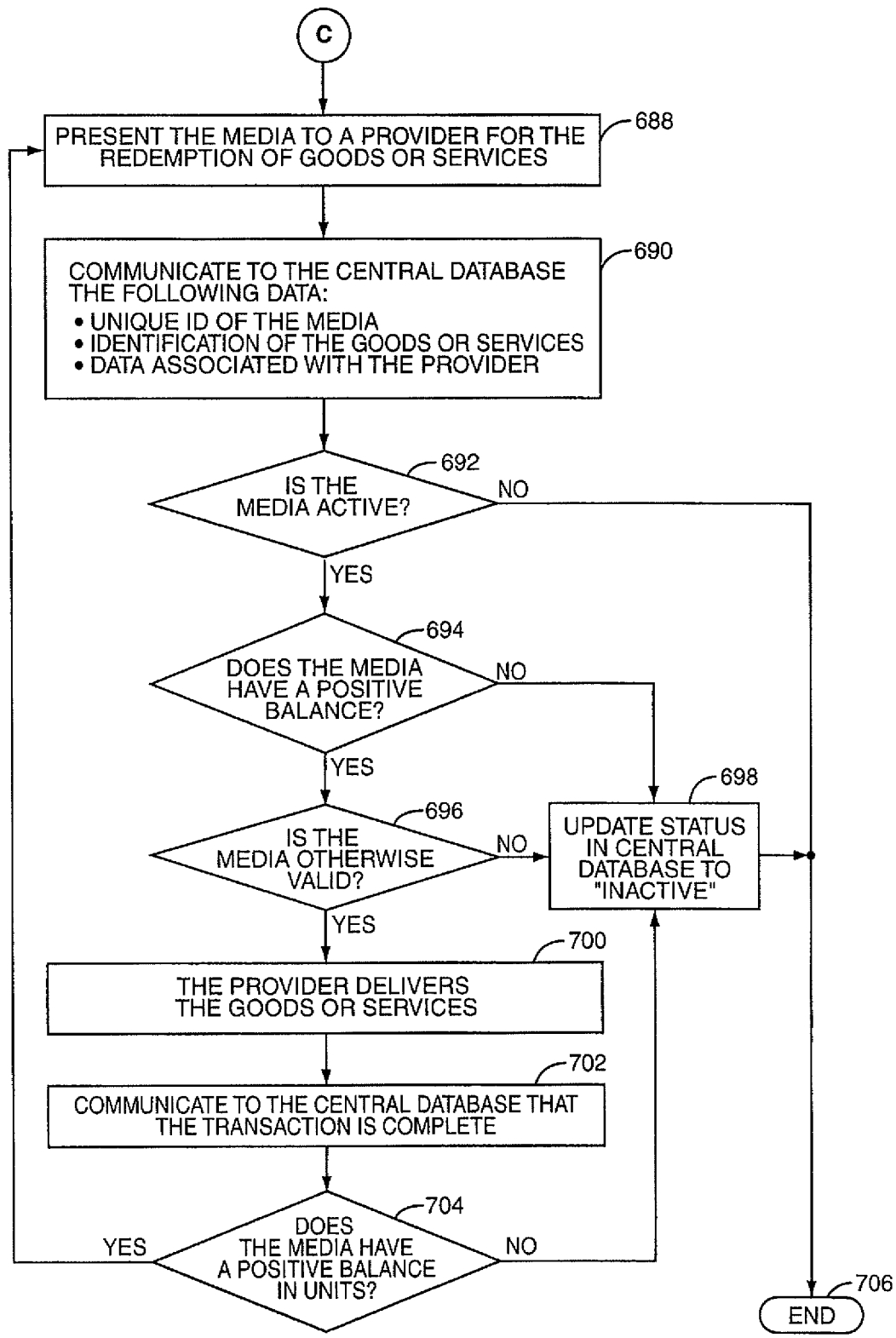

FIGS. 15A-15C also illustrate the variable value media in more detail. Prior to media activation, value units are provisioned in the central database in accordance with a set of pre-determined business rules (block 650). In this example, a variable number of value units are assigned to the media according to the method of activation and the geographic location of the providers. Optionally, a default number of value units may be assigned should the central database fail to determine the activation method. As discussed herein, the value of the media provisioned can depend on various circumstances, conditions, criteria, business rules, or some other set of pre-determined rules. Those depicted in FIGS. 15A-15C, and discussed below, are merely exemplary.

Once the rules are provisioned, an activation request is received at the central database (block 652). First, the logic at the central database would ensure that the requested media is not already active (block 654) before exercising various checks to make sure the media is still valid (block 656). If the media is already "active," or if the media is invalid, the process ends (block 658) without assigning any value units. Optionally, failures at blocks 654 and/or 656 may warrant alarm generation to alert an operator of possible fraud.

Provided the media is inactive and valid, the central database will determine the method of activation and assign value units accordingly. For instance, if activation was requested via an 8xx number (block 660) then N1 units are assigned (block 662). Otherwise, the process then checks to see if the activation was requested via the World Wide Web (block 664) and, if so, will assign N2 units (block 666). N3 units are assigned (block 670) if activation was requested via a magnetic card-reader (block 668) and N4 units (block 674) for activation via business reply mail (block 672). Of course, a default number of units, Nd, may be assigned (block 676) if the central database cannot determine how the media activation was requested. It should be noted that since, in this example, activation methods are mutually exclusive, the assignment of value units based on activation methods is also mutually exclusive. Thus, upon successful determination of the activation method, the value units are assigned accordingly and the remaining tests for activation method, if any, are bypassed. For instance, if the activation method was determined to have occurred via an 8xx number (block 660), N1 units would be assigned (block 662) to the media and execution would fall through to the tests for activation within geographic zones (block 678).

In this embodiment, variable value units according to geographic zones are assigned in addition to those assigned according to activation method. Additionally, assignment of the value units based on geographic location of activation need not be mutually exclusive, as are the activation methods. This is because zones may overlap, thereby creating the possibility of assigning value units for more than a single zone. Of course, these assignment behaviors are determined by the set of rules provisioned prior to activation requests (block 650). Thus, should the activation take place within zone one (block 678), N5 units are assigned (block 680) before checking for activation within zone two (block 682), for which N6 units are assigned (block 684). As can be seen in FIG. 15C, activation may occur in a zone that is not recognized, for instance, zone three. In this case, no value units based on geographic zone are awarded to the media. Once the value units are assigned, the media is activated by updating the media status to active in the central database (block 686).

Eventually, presentment of the media for goods or services (block 688) occurs. The provider communicates data associated with a proposed transaction (block 690) to the central database, which then uses the database to determine the status of the media (block 692). The process ends (block 706) for inactive media while active media is tested for a positive balance (block 694), and the validity of the media in general (block 696). Should the media be found to possess an inadequate balance (block 694), or be otherwise invalid (block 696), the transaction is denied by the central database, and the media status is updated to inactive (block 698) before the process ends (block 706). In contrast, should these checks succeed (blocks 692, 694, and 696), the provider delivers the goods or services (block 700) and then signals the central database that the transaction is complete (block 702). At this point, the central database will update the media's residual value (block 704), if any. As in alternate embodiments, a residual value facilitates subsequent presentments (block 688), while an inadequate residual balance results in media inactivation (block 698) before ending the process (block 706). Those skilled in the art will realize that the validity checks discussed herein are merely exemplary. The checks need not be executed in the order described, nor is the central database required to solely perform the checks. It is envisioned that at least some of the validity checks may be performed at the terminal where the media are activated.

Figure 13:
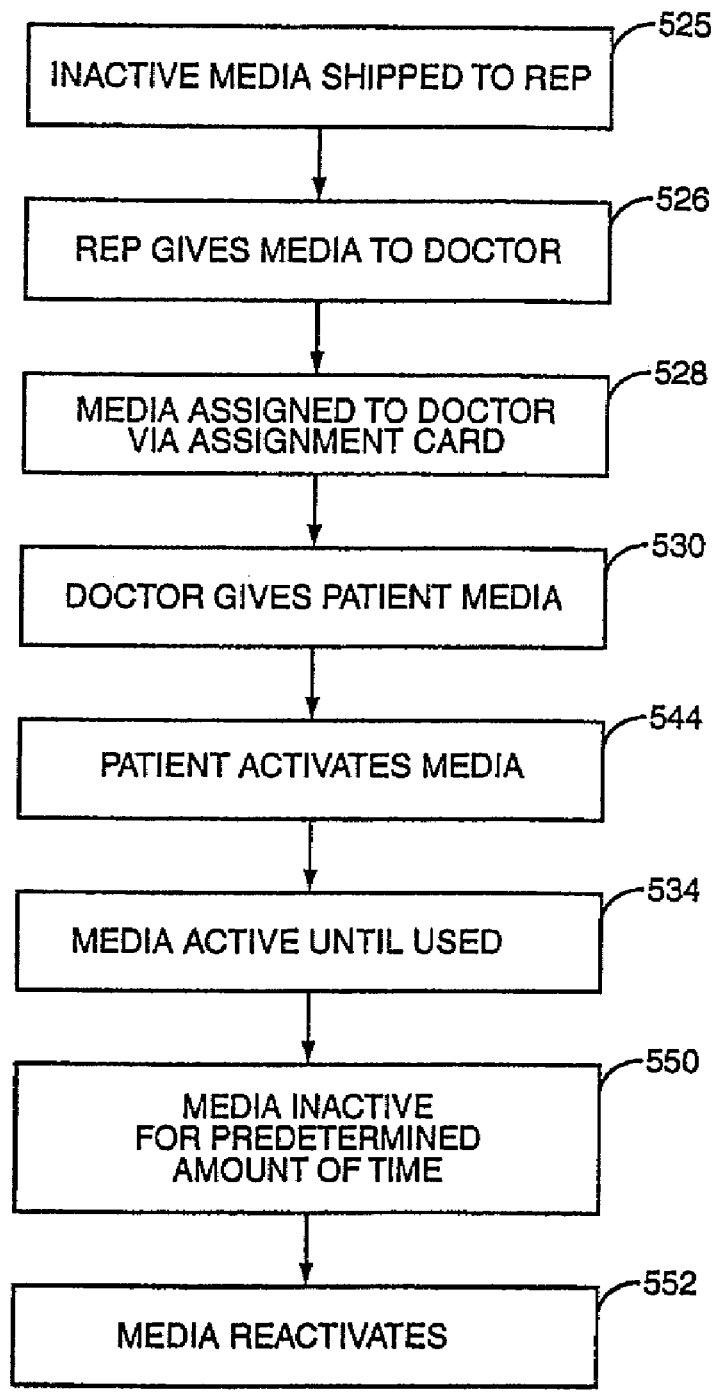

FIG. 13 illustrates a flow chart of fixed reactivated media. Specifically, the media starts out inactive and is shipped to a rep (block 525). The rep gives the media to an approved medical personnel such as a doctor (block 526). The media are assigned to the doctor via an assignment card (block 528). The media is given to a patient by the doctor (block 530). The patient activates the media via any of the approved techniques such as via the web, dialing an 800 number, replying with a business reply card, or the like (block 544). The media remains active until use at a pharmacy (block 534) and then goes inactive upon use for a designated time (block 550). The media returns to active status after a predetermined amount of time (block 552). The cycle may repeat as needed. It should be noted that other criteria besides time may be used to trigger a reactivation.

Figure 16:
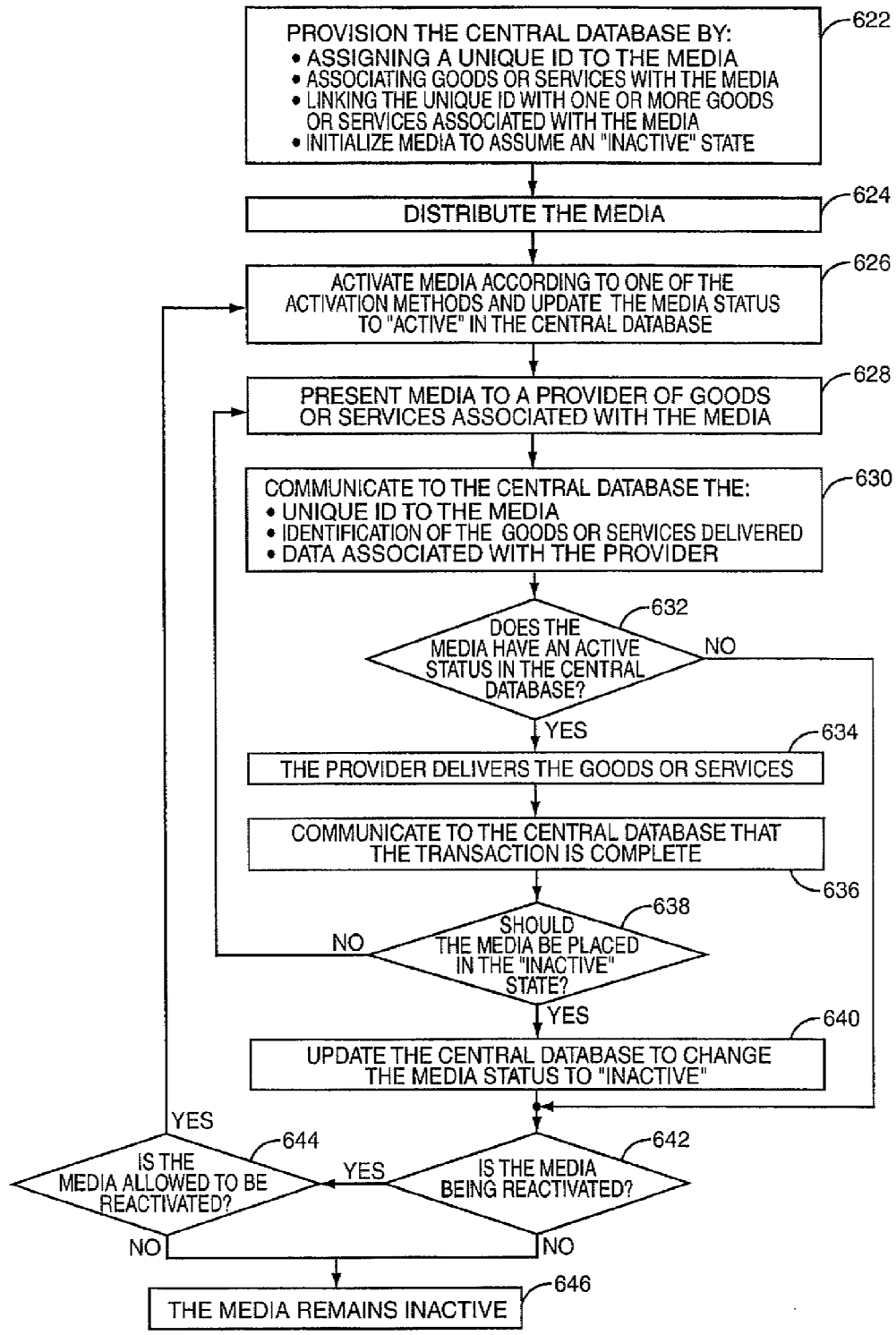
FIG. 16 is a flow chart similar to that shown in FIG. 14 but illustrating how the media can be reactivated after assuming active and inactive states.

In many instances, the central database is provisioned such that the media transitions from an inactive state to an active state, and then, after an initial presentment, returns to the inactive state. Other instances exist, however, wherein the central database is provisioned such that some media can be reactivated after the "inactive/active/inactive" cycle. This is illustrated in FIG. 16.

The reactivation process begins (block 642) at some point after the media assumes an inactive status (block 640). Reactivation can occur manually by any one of the aforementioned methods used in originally activating the media, or it can occur automatically, for instance, in response to the expiration of a timer. In this embodiment, automatic reactivation occurs when a timer, initiated at the central database in block 636, expires.

The central database, having started the timer, is notified when the timer has expired (block 642) via some mechanism designed to awaken a "sleeping" process commonly known to the art. Invalid requests, or requests received erroneously, result in the media remaining inactive (block 646). Provided the reactivation request is a valid request, however, the central database ensures that the media reactivation is authorized (block 644). Unauthorized media remains inactive (block 646) while authorized media is reactivated by updating the status in the central database to active (block 626). Manual reactivation is also possible and follows the same path as the automatic variable activation. The only difference is that the media will remain inactive until the end user manually activates the media via one of the approved aforementioned activation methods.

Further, inactive media may be reactivated upon presentment. For instance, if an end user presented an inactive media to a provider, the central database, upon reception of the transaction data (block 630), would determine that the media was inactive (block 632). In lieu of denying the proposed transaction, the central database may decide to treat this as a reactivation request (block 642). Provided the media is authorized (block 644), the media is then reactivated (block 626) and the transaction is allowed to proceed.

While the parent applications notes that the media 18 in one embodiment would be a magnetically readable card, other media are possible. For example, web based media 18 are specifically contemplated. In one example, the media 18 is a bar code or the like that is printed from a web page, much like an e-stamp, and then used with bar code readers to verify authenticity.

As noted above, the system and method of the present invention has the capability to be used in connection with the delivery and tracking of pharmaceutical and medical trial products. As discussed herein above, the media can be distributed to doctors or medical prescribers, sometimes referred to herein as "assignees." The assignees or doctors or medical prescribers will then transfer or pass out the media to patients. In the case of prescription drugs, and where the media calls for or identifies a sample prescription drug, the doctor or medical prescriber will, in one embodiment of the invention, deliver a prescription along with the media to the patient. The patient will thereafter present the media and the prescription to the pharmacy who will fill the prescription and provide the patient or the holder of the media with the corresponding value set by the media. It is important to appreciate that while the present invention is useful in a program for dispensing and tracking pharmaceutical samples, the invention can also be used to deliver and track other goods and services. It is contemplated that information and data pertaining to the product or services identified by the media as well as information and data relating to the assignees, holders and providers will be received, compiled and recorded in a central database. This will, of course, provide valuable information to manufacturers, distributors, retailers and providers of such products and services.

In creating, storing and accessing data relating to transactions surrounding the media, it is contemplated that each media will include its own unique identifier that identifies the product or service that can be redeemed or received by the selective presentment of the media. Further, either directly or indirectly, each media will identify the goods or services that may be redeemed by the media. This can be provided for directly by a code or other description. In some cases, the unique identifier that identifies the media will effectively identify the product or services redeemable by the media. In that regard, in one embodiment, data or information in the central database will effectively link or tie each media to a particular product or service. Further, the media may be provided with various advertising and/or instruction indicia or text.

As discussed above, in one embodiment of the present invention, the media is assigned to a person or other entity such as a doctor or medical prescriber, or in some cases the assignee may simply be an advertising entity, a distributor, a retailer or the like. To effectuate assignment, there may be provided assignment cards that are uniquely identified with and coupled with one or more media. Thus, in one employment of the present invention, once a single medium or a batch of media is delivered to an assignee, other person, or entity, the assignment card is utilized to transfer or direct information and data to the central database that connects or associates the media or a group of media with a particular assignee. It is appreciated that machine-readable assignment media, such as a magnetic coded card, can be utilized as an assignment card. However, in other embodiments, the assignment can simply be effectuated by a telephone call from a person or individual associated with the distribution of the media or the assignee. In one embodiment of the invention, the assignment function simply acts to connect or link one or more media with an assignee or other individual or entity that will distribute the media. In some cases, there need not be an assignment function.

As noted above, initially, the media is issued in an inactive state. Thus, in one embodiment of the present invention, the media must be activated prior to use. Eventually, individuals or other entities will come into possession of the media. These individuals are sometimes referred to as holders. In order to activate the media, the holder of the media is requested to communicate certain information to a source and that information is ultimately transferred to the central database. As discussed above, activation can take place in many ways. It can take place by the holder calling a certain phone number such as an 800 number, logging onto a particular site on a global network, responding with a business reply card, etc. Other forms of activation may be incorporated. For example, activation may occur through a machine readable device that is linked to the central database. In any event, one purpose of the activation is to connect or associate the holder with the media. Therefore, at this stage, the central database, after activation, knows the identity of the assignee, the goods or services associated with the media that are connected with the assignee, and the identity of certain holders of the media identified in the central database. In addition, the activation step can result in individual holders communicating valuable marketing information and data to the control database or to a source and ultimately to the central database.

Once the holder presents the media to a provider or pharmacy, for example, the provider may verify the authenticity of the media and determine whether the media has been activated. In many cases, the system and method will be established such that a provider such as a pharmacy will as a matter of course communicate with the central database to verify any number of parameters or conditions such as authenticity and the state of activation. This information will ultimately be recorded in the central database. Thus, when the provider dispenses a product or in the case of a service, performs a service, information will be communicated to the central database that will link the particular good or service delivered with the holder as well as other information pertaining to the media.

Underlying the present invention is the acknowledgment that understanding an individual consumer is an important marketing advantage to manufacturers, distributors and providers of products and services. By collecting data and information from individuals, this data and information enlightens manufacturers and retailers as well as service providers as to "cause and effect" and in the end provides information as to what motivates an individual consumer to purchase one product or service as opposed to purchasing another product or services. By using the data and information gathered and compiled according to the present invention, producers and marketers of goods and services are able to plan and implement advertising programs that are more focused and more directed to the consumers that matter.

The present invention has a wide area of applicability. For example, the present invention can be useful in dispensing, tracking and generally managing any type of sample or trial product program such as a pharmaceutical sample program. Further, the method and system of the present invention can be used in product loyalty programs, co-pay programs where a third party, such as a pharmaceutical company, participates to make a prescription co-payment for the consumer, patient assistance programs that are sponsored by pharmaceutical companies, and in general is applicable to promoting and advertising goods and services of all types. In the preceding disclosure, a number of examples have been presented wherein the good or product being delivered via the medium is a prescription drug or pharmaceutical product. It should be understood, however, that the present invention can be utilized to promote or deliver any good or service.

Figure 17:
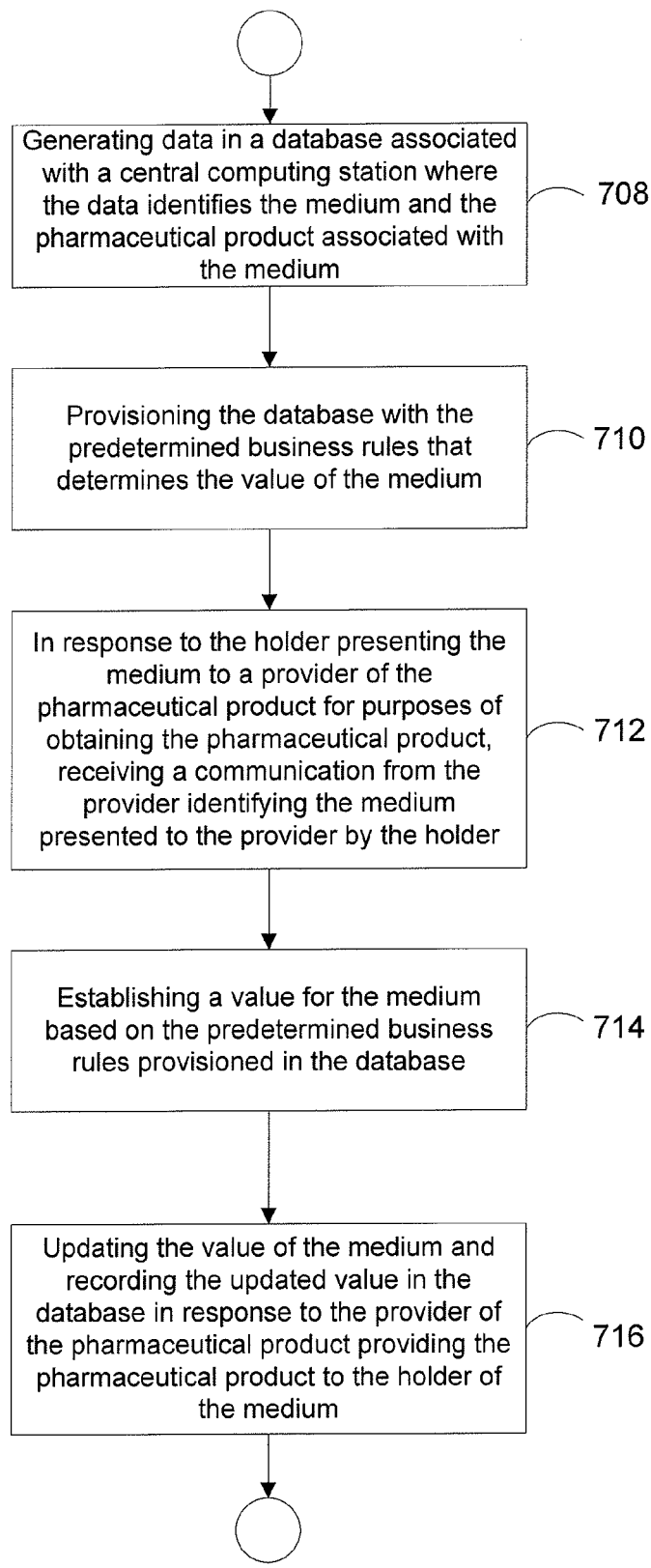
FIG. 17 is a flow chart showing a method of delivering a pharmaceutical product via a medium, according to one or more embodiments.

FIG. 17 illustrates a method of delivering a pharmaceutical product via a medium, according to one or more embodiments. The pharmaceutical product is associated with the medium and the medium assumes different values based on predetermined business rules. The method comprises generating data in a database associated with a central computing station where the data identifies the medium and the pharmaceutical product associated with the medium (block 708). The method further comprises provisioning the database with the predetermined business rules that determines the value of the medium (block 710). The method also comprises, in response to the holder presenting the medium to a provider of the pharmaceutical product for purposes of obtaining the pharmaceutical product, receiving a communication from the provider identifying the medium presented to the provider by the holder (block 712). Moreover, the method comprises establishing a value for the medium based on the predetermined business rules provisioned in the database (block 714). The method further comprises updating the value of the medium and recording the updated value in the database in response to the provider of the pharmaceutical product providing the pharmaceutical product to the holder of the medium (block 716).

Figure 18:
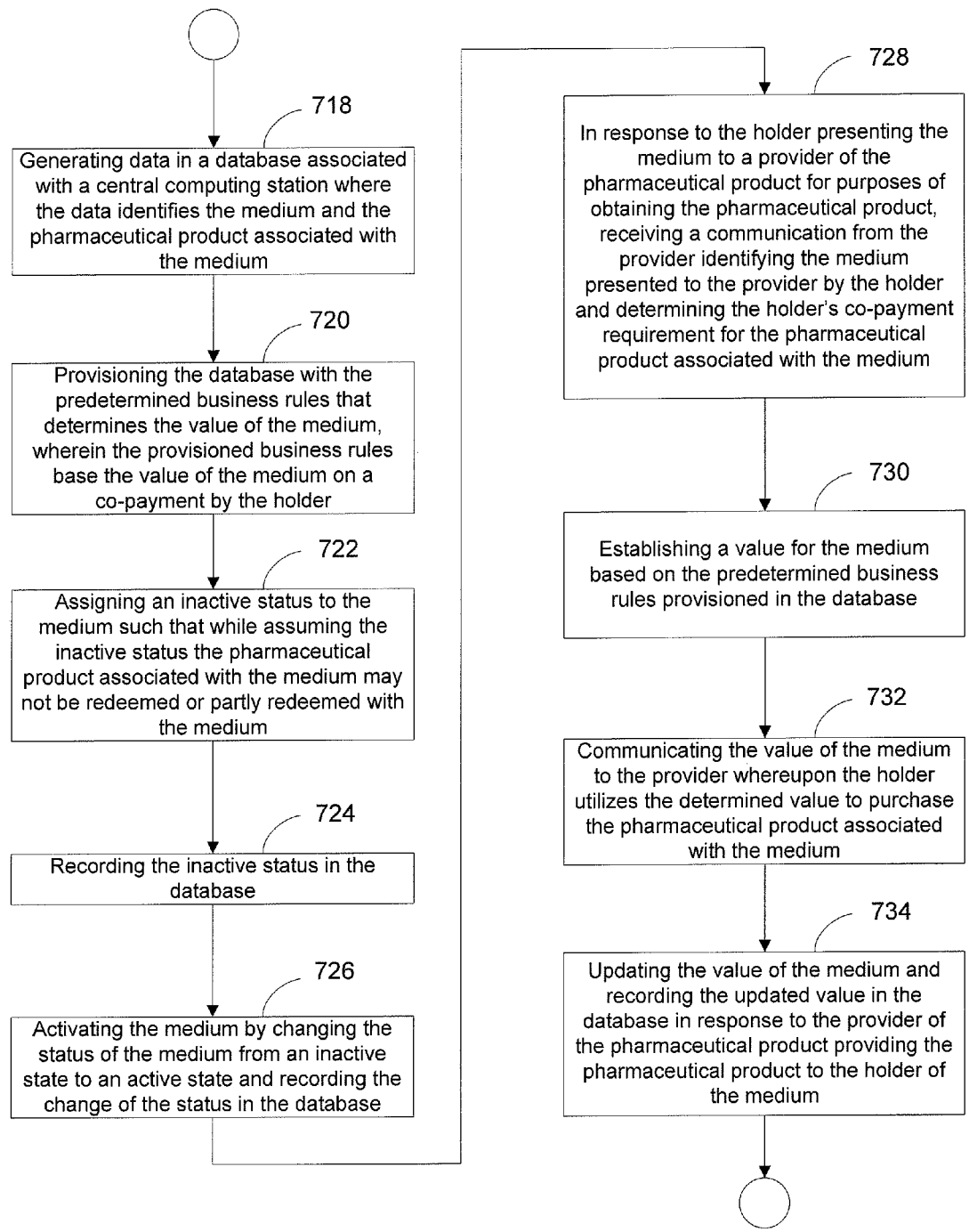
FIG. 18 is a flow chart showing a method of delivering a pharmaceutical product via a medium, according to one or more other embodiments.

FIG. 18 illustrates a method of delivering a pharmaceutical product via a medium, according to one or more other embodiments. Again, the pharmaceutical product is associated with the medium and the medium assumes different values based on predetermined business rules. The method comprises generating data in a database associated with a central computing station where the data identifies the medium and the pharmaceutical product associated with the medium (block 718). The method further comprises provisioning the database with the predetermined business rules that determines the value of the medium, wherein the provisioned business rules base the value of the medium on a co-payment by the holder (block 720).

The method also comprises assigning an inactive status to the medium such that while assuming the inactive status the pharmaceutical product associated with the medium may not be redeemed or partly redeemed with the medium (block 722). The method further comprises recording the inactive status in the database (block 724). Still further, the method comprises activating the medium by changing the status of the medium from an inactive state to an active state and recording the change of the status in the database (block 726).

The method also comprises, In response to the holder presenting the medium to a provider of the pharmaceutical product for purposes of obtaining the pharmaceutical product, receiving a communication from the provider identifying the medium presented to the provider by the holder and determining the holder's co-payment requirement for the pharmaceutical product associated with the medium (block 728). Moreover, the method comprises establishing a value for the medium based on the predetermined business rules provisioned in the database (block 730). The method also includes communicating the value of the medium to the provider whereupon the holder utilizes the determined value to purchase the pharmaceutical product associated with the medium (block 732). The method further comprises updating the value of the medium and recording the updated value in the database in response to the provider of the pharmaceutical product providing the pharmaceutical product to the holder of the medium (block 734).

The present invention may, of course, be carried out in other specific ways than those herein set forth without departing from the scope and the essential characteristics of the invention. The present embodiments are therefore to be construed in all aspects as illustrative and not restrictive and all changes coming within the meaning and equivalency range of the appended claims are intended to be embraced therein.

What is claimed is:

1. A method of delivering a pharmaceutical product via a medium where the pharmaceutical product is associated with the medium and the medium assumes different values based on predetermined business rules, the method comprising:
   generating data in a database associated with a central computing station where the data identifies the medium and the pharmaceutical product associated with the medium;
   provisioning the database with the predetermined business rules that determines the value of the medium;
   in response to a holder presenting the medium to a provider of the pharmaceutical product for purposes of obtaining the pharmaceutical product, receiving at the central computing station a communication from the provider identifying the medium presented to the provider by the holder;
   establishing a value for the medium, using the central computing station, based on the predetermined business rules provisioned in the database; and
   updating the value of the medium and recording the updated value in the database, using the central computing station, in response to the provider of the pharmaceutical product providing the pharmaceutical product to the holder of the medium.

2. The method of claim 1 wherein the provisioned business rules that determine the value of the medium base the value of the medium on a co-payment of the holder.

3. The method of claim 1 wherein the value of the medium varies with a co-payment of the holder and wherein the method includes in response to the holder presenting the medium to the provider, determining the holder's co-payment for the pharmaceutical product associated with the medium.

4. The method of claim 1 further comprising communicating the value of the medium to the provider whereupon the holder utilizes the medium to purchase the pharmaceutical product associated with the medium.

5. The method of claim 1 wherein initially the medium assumes an inactive state and wherein subsequently the medium assumes an active state, and wherein the medium in an inactive state is ineffective to purchase the pharmaceutical product associated with the medium.

6. The method of claim 1 including recording a unique identifier in the database where the unique identifier is associated with the medium.

7. The method of claim 1 further including:
   assigning an inactive status to the medium such that while assuming the inactive status the pharmaceutical product associated with the medium may not be redeemed or partly redeemed with the medium;
   recording the inactive status in the database; and
   activating the medium by changing the status of the medium from an inactive state to an active state and recording the change of the status in the database.

8. The method of claim 1 wherein the value of the medium varies with a co-payment of the holder and wherein the method includes in response to the holder presenting the medium to the provider, determining the holder's co-payment for the pharmaceutical product associated with the medium; and communicating the value of the medium to the provider whereupon the holder utilizes the value to purchase the pharmaceutical product associated with the medium.

9. The method of claim 8 further including:
   assigning an inactive status to the medium such that while assuming the inactive status the pharmaceutical product associated with the medium may not be redeemed or partly redeemed with the medium;
   recording the inactive status in the database; and
   activating the medium by changing the status of the medium from an inactive state to an active state and recording the change of the status in the database.

10. The method of claim 1 wherein based on the medium and the business rules provisioned in the database, communicating the value of the medium to the provider whereupon the holder utilizes the value to purchase the pharmaceutical product associated with the medium; and wherein initially the medium assumes an inactive state and wherein subsequently the medium assumes an active state, and wherein the medium in an inactive state is ineffective to purchase the pharmaceutical product associated with the medium.

11. The method of claim 10 including recording a unique identifier in the database where the unique identifier is associated with the medium.

\* \* \* \* \*